United States Patent
Kates et al.

(10) Patent No.: US 11,123,357 B2
(45) Date of Patent: *Sep. 21, 2021

(54) METHODS AND COMPOSITIONS FOR TREATING ORAL MUCOSITIS

(71) Applicant: Lakewood Amedex, Inc., Sarasota, FL (US)

(72) Inventors: Steven A. Kates, Needham, MA (US); Steven Parkinson, University Park, FL (US); Patrick C. O'Connor, University Park, FL (US)

(73) Assignee: Lakewood Amedex, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/656,129

(22) Filed: Oct. 17, 2019

(65) Prior Publication Data

US 2020/0121708 A1  Apr. 23, 2020

Related U.S. Application Data

(60) Provisional application No. 62/746,943, filed on Oct. 17, 2018.

(51) Int. Cl.
| | | |
|---|---|---|
| *A61K 31/7072* | (2006.01) | |
| *A61P 31/04* | (2006.01) | |
| *A61K 9/00* | (2006.01) | |
| *A61K 45/06* | (2006.01) | |

(52) U.S. Cl.
CPC .......... *A61K 31/7072* (2013.01); *A61K 9/006* (2013.01); *A61K 9/0056* (2013.01); *A61P 31/04* (2018.01); *A61K 45/06* (2013.01)

(58) Field of Classification Search
CPC .. A61K 31/7072; A61K 9/006; A61K 9/0056; A61P 31/04
See application file for complete search history.

(56) References Cited

U.S. PATENT DOCUMENTS

| | | |
|---|---|---|
| 4,421,769 A | 12/1983 | Dixon et al. |
| 5,167,950 A | 12/1992 | Lins |
| 5,824,666 A | 10/1998 | Deckner et al. |
| 6,211,349 B1 | 4/2001 | Dale et al. |
| 6,521,213 B1 | 2/2003 | Mautone |
| 7,314,923 B2 | 1/2008 | Kaneko et al. |
| 7,868,162 B2 | 1/2011 | Dale |
| 2005/0232891 A1 | 10/2005 | Moloney et al. |
| 2009/0233879 A1 | 9/2009 | Reddy et al. |
| 2011/0135713 A1 | 6/2011 | Dale |
| 2011/0201674 A1 | 8/2011 | Schramm et al. |
| 2016/0120936 A1 | 5/2016 | Troxel |
| 2016/0166498 A1 | 6/2016 | Anastassov et al. |
| 2016/0271217 A1 | 9/2016 | Gronberg et al. |

FOREIGN PATENT DOCUMENTS

| | | |
|---|---|---|
| WO | 0040591 A1 | 7/2000 |
| WO | 0057890 A1 | 10/2000 |
| WO | 02089581 A1 | 11/2002 |
| WO | 2008133704 A1 | 11/2008 |
| WO | 2012017434 A2 | 2/2012 |
| WO | 2014124430 A1 | 8/2014 |
| WO | 2018231863 A1 | 12/2018 |

OTHER PUBLICATIONS

Donnelly et al., Lancet Infect. Dis., 2003, 3, p. 405-412. (Year: 2003).*
International Search Report and Written Opinion; International Application No. PCT/US18/22068; dated Jun. 1, 2018; 7 pages.
International Preliminary Report on Patentability; International Application No. PCT/US18/22068; dated Sep. 19, 2019; 5 pages.
International Search Report and Written Opinion; International Application No. PCT/US18/22071; dated Jul. 3, 2018; 10 pages.
International Preliminary Report on Patentability; International Application No. PCT/US18/22071; dated Sep. 19, 2019; 6 pages.
Lidia Chomicz et al.; The Radiosensitivity of 5- and 6-Bromocytidine Derivatives—Electron Induced DNA Degradation; Phys. Chem. Chem. Phys.; 2014; 16; pp. 19424-19428; Royal Society of Chemistry.
Lidia Chomicz et al.; Electron Induced Single Strand Break and Cyclization: A DFT Study on the Radiosensitization Mechanism of the Nucleotide of 8-Bromoguanine; Physical Chemistry Chemical Physics; 2014; 16; pp. 6568-6574; Royal Society of Chemistry.
Subhrangsu Chatterjee et al.; The Chemical Nature of the 2'-Substituent in the Pentose-Sugar Dictates the Pseudoaromatic Character of the Nucleobase (pKa) in DNA/RNA; Organic & Biomolecular Chemistry; 2006; 4; pp. 1675-1686; Royal Society of Chemistry.
Jharna Barman et al.; Non-Identical Electronic Characters of the Internucleotidic Phosphates in RNA Modulate the Chemical Reactivity of the Phosphodiester Bonds; Organic & Biomolecular Chemistry; 2006; 4; pp. 928-941; Royal Society of Chemistry.
P. Acharya et al.; Measurement of Nucleobase pKa Values in Model Mononucleotides Shows RNA-RNA Duplexes to be More Stable Than DNA-DNA Duplexes; Journal of the American Chemical Society; 2004; 126, pp. 2862-2869; American Chemical Society.
Matjaz Polak et al.; The Change in the Electronic Character Upon Cisplatin Binding to Guanine Nucleotide is Transmitted to Drive the Conformation of the Local Sugar-Phosphate Backbone—A Quantitative Study; Journal of the Chemical Society; Perkins Translations I; 1999; pp. 2835-2843; The Royal Society of Chemistry.
Erathodiyil Nandanan et al.; Structure-Activity Relationships of Bisphosphate Nucleotide Derivatives as P2Y1 Receptor Antagonists and Partial Agonists; Journal of Medical Chemistry; 1999; 42; pp. 1625-1638; American Chemical Society.
Cornelis S.M. Olsthoorn et al.; Conformational Characteristics of the Trinucleoside Diphosphate dApdApdA and its Constituents From Nuclear Magnetic Resonance and Circular Dichroism Studies; European Journal of Biochemistry; 112; 1980; pp. 95-110.
Stephen M. Berge et al., Pharmaceutical Salts; Journal of Pharmaceutical Sciences; Jan. 1977; 19 pages; vol. 66, No. 1.
D. Lison et al., Update on the Genotoxicity and Carcinogenicity of Cobalt Compounds; Occup Environ Med; 2001; 7 pages; vol. 58.

(Continued)

*Primary Examiner* — Jonathan S Lau
(74) *Attorney, Agent, or Firm* — Taft Stettinius & Hollister LLP; Ryan P. Hiler, Esq.

(57) ABSTRACT

Methods and pharmaceutical compositions including Bisphosphocins for treating oral mucositis in a patient are disclosed.

21 Claims, 5 Drawing Sheets

(56) References Cited

OTHER PUBLICATIONS

Pradeep Tyagi et al.; Recent Advances in Intravesical Drug/Gene Delivery; Molecular Pharmaceutics; Jan. 3, 2006; 11 pages; vol. 3, No. 4.
Michael D. Melekos et al.; Complicated Urinary Tract Infections; Elsevier; International Journal of Antimicrobial Agents; 2000; 10 pages; vol. 15.
Susanna Valanne et al.; CAMP Factor Homologues in Propionibacterium Acnes: A New Protein Family Differentially Expressed by Types I and II; Microbiology; May 1, 2005; 11 pages; vol. 151.
N.S. Jagtap et al.; Development and Evaluation of Herbal Wound Healing Formulations; International Journal of PharmTech Research; Oct.-Dec. 2009; 5 pages; vol. 1, No. 4.
Liane I.F. Moura et al.; Recent Advances on the Development of Wound Dressings for Diabetic Foot Ulcer Treatment—A Review; Elsevier; Acta Biomaterialia, Jul. 2013; 22 pages; vol. 9, No. 7.
Vijay D. Wagh et al.; Formulation and Evaluation of in situ Gel Drug Delivery System of Sesbania grandiflora Flower Extract for the Treatment of Bacterial Conjunctivitis; Journal of Pharmaceutical Sciences and Research; 2012; 5 pages; vol. 4, No. 8.
Pelin Aksungur et al.; Chitosan Delivery Systems for the Treatment of Oral Mucositis: In Vitro and In Vivo Studies; Elsevier; Journal of Controlled Release; Aug. 11, 2004; 12 pages; vol. 98, No. 2.
Xiaowei Feng et al.; Efficacy and Tolerability of Amorolfine 5% Nail Lacquer in Combination with Systemic Antifungal Agents for Onychomycosis: A Meta-Analysis and Systematic Review; Wiley; Dermatologic Therapy; Jan. 18, 2017; 6 pages; vol. 30, No. 3.
International Search Report and Written Opinion; International Application No. PCT/US2018/037151; dated Aug. 28, 2018; 14 pages.
International Preliminary Report on Patentability; International Application No. PCT/US2018/037151; dated Dec. 17, 2019; 12 pages.
First Office Action and Search Report; Chinese Application No. 201880030624.4; dated Nov. 2, 2020; 11 pages.
Extended European Search Report; European Application No. 18763136.1; dated Dec. 15, 2020; 13 pages.
Mason, Jennifer M. et al., Oligonucleotide transition state analogues of saporin L3, European Journal of Medicinal Chemistry, 127, 2017, pp. 793-809, Elsevier Masson SAS.
Abramova, Tatyana V. et al., Synthesis of nucleotide-amino acid conjugates designed for photo-CIDNP experiments by a phosphotriester approach, Beilstein Journal of Organic Chemistry, 9, 2013, pp. 2898-2909.
International Search Report and Written Opinion; Patent Cooperation Treaty; International Application No. PCT/US2019/056772; dated Dec. 27, 2019; 10 pages.

\* cited by examiner

METHODS AND COMPOSITIONS FOR TREATING ORAL MUCOSITIS

CROSS REFERENCE TO RELATED APPLICATIONS

This application claims priority to U.S. Provisional Patent Application Ser. No. 62/746,943 filed on Oct. 17, 2018, which is incorporated by reference herein in its entirety.

FIELD

The present disclosure relates generally to the use of Bisphosphocins for the prevention and treatment of oral mucositis in patient.

BACKGROUND

Oral mucositis is a condition characterized by inflammation and ulceration in the mouth. Oral mucositis is a common complication experienced by patients receiving cancer chemotherapy or radiation treatment. Oral mucositis can lead to several problems, including pain, nutritional problems as a result of inability to eat, and increased risk of infection due to open sores in the mucosa. Oral mucositis may also have a significant effect on a cancer patient's quality of life and can limit the effectiveness of certain treatment options (i.e., requiring a reduction in subsequent chemotherapy doses). Oral mucositis is also a significant side effect of bone marrow transplantation.

Clinically, mucositis progresses through three stages, including (1) early, painful mucosal erythema, which can be palliated with local anesthetics or non-narcotic analgesics; (2) painful ulceration with pseudomembrane formation, and pain is often of such intensity as to require parenteral narcotic analgesia; and (3) spontaneous healing, occurring about 2-4 weeks after cessation of anti-neoplastic therapy.

Oral mucositis is generally difficult to treat and not adequately managed by current approaches. Current estimates indicate that over 500,000 patients suffer from oral mucositis annually in the United States alone. Given that patients often receive multiple cycles of chemo- and/or radiotherapy, there are estimated to be over 1,000,000 incidences of oral mucositis per year in the United States. The incidence of oral mucositis varies depending on the type of tumor, age of the patient, and state of oral health. The therapies used in these different tumor types are an important factor with aggressive chemotherapy protocols being associated with a higher incidence of oral mucositis. Younger patients also have a higher incidence of oral mucositis, which may be due to their more rapid epithelial cell turnover and, hence, susceptibility to cytotoxic drugs.

Current approaches for the treatment and prevention of oral mucositis are suboptimal. The most common approaches include oral hygiene protocols, anti-inflammatory agents, and cryoprotective agents. Biological response modulators and physical therapies (such as cryotherapy and laser treatments) are also used with mixed results. Each of these approaches have been met with limited success. For example, the use of an allopurinol mouthwash, an oral sucralfate slurry, and pentoxifylline were reported in preliminary studies to result in a decrease in oral mucositis. Subsequent randomized and controlled studies, however, have failed to demonstrate any benefit of treatment with these agents. Furthermore, chlorhexidine, an antimicrobial mouth rinse, has been used extensively in the treatment and prevention of oral mucositis. Notably, however, the efficacy of chlorhexidine is significantly decreased in saliva, and this compound is also relatively ineffective against the Gram negative bacteria that tend to colonize the oral cavity in patients undergoing radiation therapy. In addition, at least one study has shown that the use of chlorhexidine may be detrimental and result in a higher incidence of mucositis. Further, several studies have shown that the use of a vancomycin paste and antibiotic lozenges containing polymixin B, tobramycin and amphotericin B in patients undergoing myelosuppresive chemotherapy or radiation therapy can result in a decrease in oral mucositis and in the incidence of sepsis due to alpha hemolytic streptococci.

Current therapy for mucositis is predominantly palliative and focused on pain control and maintenance of nutrition. However, recent data indicates that even opioids are often insufficient to control mucositis pain. Currently, the only approved treatment for oral mucositis is palifermin (Kepivance®), and its application is limited to mucositis in patients undergoing conditioning regimens prior to hematopoietic stem cell transplant.

The complexity of mucositis as a biological process continues to be defined. It has been suggested that the condition represents a sequential interaction of oral mucosal cells and tissues, reactive oxygen species, pro-inflammatory cytokines, mediators of apoptosis, and local factors such as saliva and the oral microbiota. While epithelial degeneration and breakdown ultimately result in mucosal ulceration, it appears that the early changes associated with radiation-induced mucosal toxicity occur within the endothelium, and connective tissue of the submucosa. Electron microscopic evaluation of mucosa within 1 week of radiation shows damage to both endothelium and connective tissue, but not epithelium. Such injury is likely to be mediated by free radical formation. It appears that the overall mechanism for mucositis development is similar for both radiation and chemotherapy. There is no data to support a direct bacterial etiology for mucositis. Data suggest that the bacterial load of ulcerative lesions trails the development of lesions suggesting secondary colonization.

Topical application of agents useful to treat oral diseases such as oral mucositis presents unique problems. For example, due to salivation and/or food or fluid intake, it is oftentimes extremely difficult to attain sufficient mucoadhesion and residence time in the mouth for the agent to be effective. Topical application of peptides is even more problematic, as the peptides must be stable to proteolytic enzymes resident in saliva. Other difficulties associated with topical oral application of drugs include tooth discoloration and patient compliance. Oral pharmaceutical compositions providing good mucoadhesion and residence time in the mouth while at the same time providing high levels of patient compliance are not readily available. None of the current treatment or prevention options for oral mucositis are viewed as conclusively effective.

Although strategies are available for addressing the above-mentioned problems regarding oral mucositis, such strategies are inconvenient and have significant have drawbacks. Accordingly, a need remains for better options for preventing and treating oral mucositis.

SUMMARY

The present disclosure provides methods of treating oral mucositis in a patient in need thereof that address the problems and need detailed above. In some embodiments, the method comprises administering an effective amount of a Bisphosphocin, or a pharmaceutically acceptable salt thereof, to the patient. In some embodiments, the Bisphosphocin is selected from the group consisting of Nu-2, Nu-3, Nu-4, Nu-5, and Nu-8.

In some embodiments, the administration is topical administration. In some embodiments, the topical administration is applied to the oral cavity of the patient.

In some embodiments, the administration is carried out using the Bisphosphocin in a gel, ointment, oil, solution, suspension, emulsion or other viscous composition. In some embodiments, the administration is carried out using the Bisphosphocin in a mouthwash. In some embodiments, the patient is administered at least one additional active ingredient. In some embodiments, the Bisphosphocin is administered with a pharmaceutically acceptable carrier.

In some embodiments, the administration is carried out as a multiple dose regimen. In some embodiments, the administration is carried out one or more times per day. In some embodiments, the patient is a human.

Another aspect of the present disclosure provides a method of treating oral mucositis in a patient in need thereof. In some embodiments, the method comprises topically administering to the oral cavity of the patient an effective amount of a pharmaceutical composition comprising a Bisphosphocin, or a pharmaceutically acceptable salt thereof, and a pharmaceutically acceptable carrier. In some embodiments, the Bisphosphocin is selected from the group consisting of Nu-2, Nu-3, Nu-4, Nu-5, and Nu-8.

In some embodiments, the administration is carried out using the Bisphosphocin in a gel, ointment, oil, solution, suspension, emulsion or other viscous composition. In some embodiments, the administration is carried out using the Bisphosphocin in a mouthwash.

In some embodiments, the Bisphosphocin is present in the pharmaceutical composition in an amount from about 1% to about 20% (weight/weight). In some embodiments, the Bisphosphocin is present in the pharmaceutical composition in an amount from about 5% to about 15% (weight/weight). In some embodiments, the Bisphosphocin is present in the pharmaceutical composition in an amount from about 30% to about 50% (weight/weight).

In some embodiments, the administration is carried out as a multiple dose regimen. In some embodiments, the administration is carried out one or more times per day. In some embodiments, the patient is a human.

Another aspect of the present disclosure provides a pharmaceutical composition for treating oral mucositis comprising a Bisphosphocin, or a pharmaceutically acceptable salt thereof, and a pharmaceutically acceptable carrier. In some embodiments, the Bisphosphocin is selected from the group consisting of Nu-2, Nu-3, Nu-4, Nu-5, and Nu-8.

In some embodiments, the Bisphosphocin is present in the pharmaceutical composition in an amount from about 1% to about 20% (weight/weight). In some embodiments, the Bisphosphocin is present in the pharmaceutical composition in an amount from about 5% to about 15% (weight/weight). In some embodiments, the Bisphosphocin is present in the pharmaceutical composition in an amount from about 30% to about 50% (weight/weight).

In some embodiments, the pharmaceutically acceptable carrier is a diluent. In some embodiments, the diluent is selected from water, glycerol, mannitol, and saline. In some embodiments, the saline is phosphate buffered saline.

In some embodiments, the diluent is present in the pharmaceutical composition in an amount from about 1% to about 10% (weight/weight). In some embodiments, the diluent is present in the pharmaceutical composition in an amount from about 1% to about 15% (weight/weight). In some embodiments, the diluent is present in the pharmaceutical composition in an amount from about 1% to about 20% (weight/weight).

Another aspect of the present disclosure provides a method of treating oral mucositis in a patient in need thereof. In some embodiments, the method comprises topically administering to the oral cavity of the patient an effective amount of the pharmaceutical composition of the present disclosure.

In some embodiments, the pharmaceutical composition has a pH of about pH 1.5 to about pH 4. In some embodiments, the pharmaceutical composition has a pH of about pH 3 to about pH 4.

Another aspect of the present disclosure provides a Bisphosphocin selected from the group consisting of Nu-2, Nu-3, Nu-4, Nu-5, and Nu-8, or a pharmaceutically acceptable salt thereof, for use in treating oral mucositis.

Another aspect of the present disclosure provides a use of a Bisphosphocin, or a pharmaceutically acceptable salt thereof, for the manufacture of a medicament for treating oral mucositis.

Another aspect of the present disclosure provides a pharmaceutical composition comprising a Bisphosphocin selected from the group consisting of Nu-2, Nu-3, Nu-4, Nu-5, and Nu-8, or a pharmaceutically acceptable salt thereof, and a pharmaceutically acceptable carrier for use in treating oral mucositis.

Another aspect of the present disclosure provides a use of a pharmaceutical composition comprising a Bisphosphocin selected from the group consisting of Nu-2, Nu-3, Nu-4, Nu-5, and Nu-8, or a pharmaceutically acceptable salt thereof, and a pharmaceutically acceptable carrier for the manufacture of a medicament for treating oral mucositis.

One advantage of a method and/or pharmaceutical composition according to an embodiment of the present disclosure is that the mechanism of action of the activity of a compound of the present disclosure is effective against many different clinically relevant pathogenic bacteria, including both gram positive and gram negative. Another advantage of a method and/or pharmaceutical composition according to an embodiment of the present disclosure is that a compound of the present disclosure according to an embodiment is non-toxic to a patient treated with an effective amount of a compound of the present disclosure.

Another advantage of method and/or pharmaceutical composition containing a compound of the present disclosure is that such compound is relatively fast acting and, therefore, does not need to be in contact with mucosal sores for more than typical durations effective for clinical or daily oral hygiene, typically in the range of 10 seconds up to 5 minutes, though longer treatment times may be used.

A further advantage of a method and/or pharmaceutical composition according to an embodiment of the present disclosure is that such method and/or pharmaceutical composition is useful for treating infections caused by biofilms. Such infections caused by biofilms are described in Oral mucositis caused by *Candida glabrate* biofilms. Another advantage of a pharmaceutical composition according to an embodiment of the present disclosure is that such pharmaceutical composition can be used during or after chemotherapeutic treatment.

These and other objects, advantages, and features of the present disclosure will become apparent to those skilled in the art upon reading the details of the compounds and pharmaceutical compositions according to the present disclosure and uses thereof as more fully described below.

BRIEF DESCRIPTION OF THE DRAWINGS

The teachings of some embodiments of the present invention will be better understood by reference to the description taken in conjunction with the accompanying drawings, wherein.

DETAILED DESCRIPTION

Figure 1A:
FIG. 1A shows a mucositis score of zero (0) for an animal.
Figure 1B:
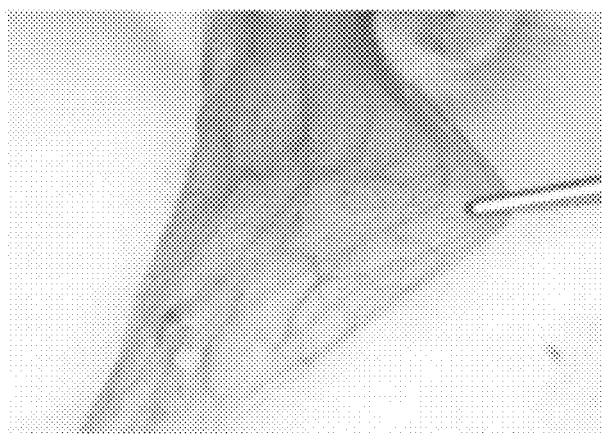
FIG. 1B shows a mucositis score of one (1) for an animal.
Figure 1C:
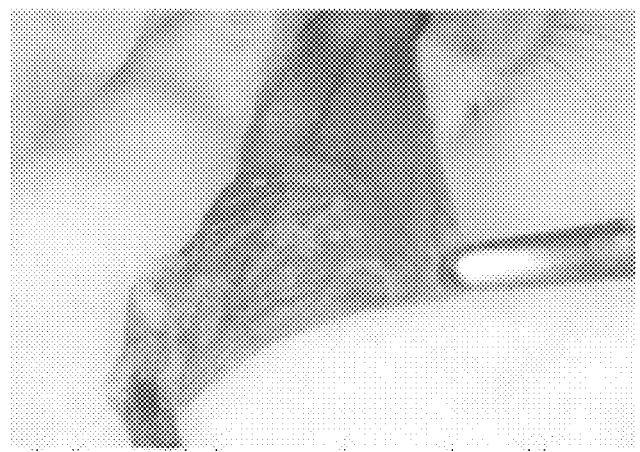
FIG. 1C shows a mucositis score of two (2) for an animal.
Figure 1D:
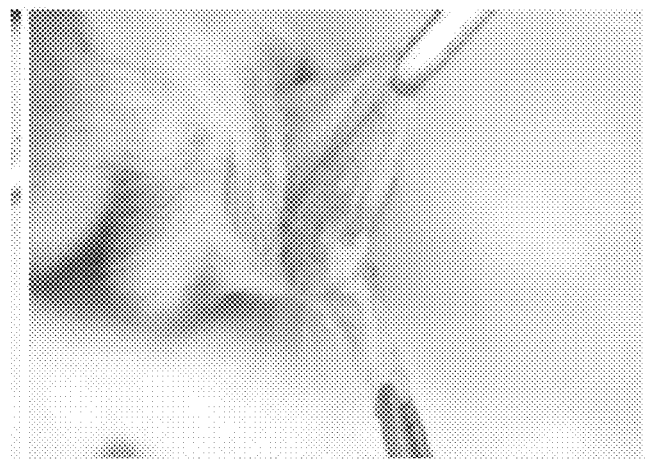
FIG. 1D shows a mucositis score of three (3) for an animal.
Figure 1E:
FIG. 1E shows a mucositis score of four (4) for an animal.
Figure 1F:
FIG. 1F shows a mucositis score of five (5) for an animal.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

The present disclosure provides a method of controlling oral mucositis in a patient in need thereof. In some embodiments, an effective amount of a Bisphosphocin, or a pharmaceutically acceptable salt thereof, is administered to the patient.

As used herein, the term "Bisphosphocin" refers to a class of chemical compounds having antimicrobial activity, including Nu-2, Nu-3, Nu-4, Nu-5, and Nu-8, or a pharmaceutically acceptable salt thereof. U.S. Pat. Nos. 6,627,215; 6,211,162; 7,868,162; 7,176,191; 8,435,960; and 6,211,349; and U.S. Patent Application Publication Numbers 2017-0191062; 2018-0258128; and 2018-0353529, all of which are hereby incorporated by reference in their entireties, disclose Bisphosphocins and how to make and use Bisphosphocins. The terms "Bisphosphocin" and a "compound of the present disclosure" are used interchangeably herein.

The chemical name of Nu-2 is ((2R,3R,4R,5R)-5-(2,4-dioxo-3,4-dihydropyrimidin-1(2H)-yl)-3-((hydroxy(4-hydroxybutoxy)phosphoryl)oxy)-4-methoxytetrahydrofuran-2-yl)methyl (4-hydroxybutyl) hydrogen phosphate. The molecular formula of Nu-2 is $C_{18}H_{32}N_2O_{14}P_2$. Nu-2 has the following formula:

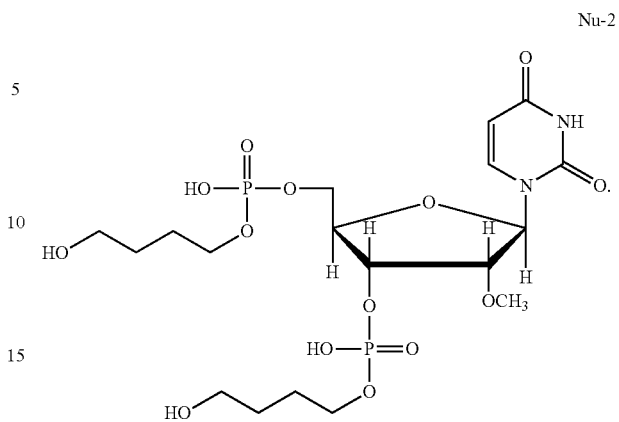

The chemical name of Nu-3 is (2R,3S)-2-((butoxy(hydroxy)phosphoryl)oxy)methyl)-5-(5-methyl-2,4-dioxo-3,4-dihydropyrimidin-1(2H)-yl)tetrahydrofuran-2-yl) butyl hydrogen phosphate. The molecular formula of Nu-3 is $C_{18}H_{32}N_2O_{11}P_2$. Nu-3 has the following formula:

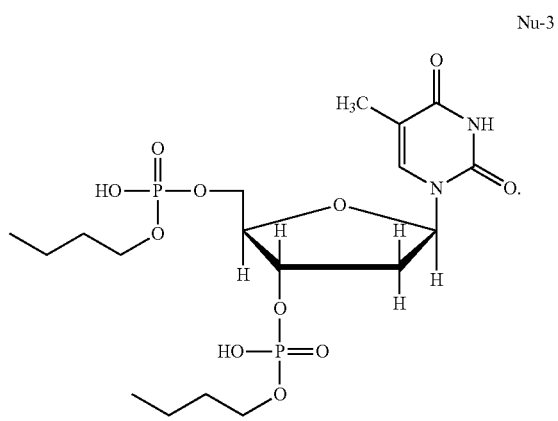

The chemical name of Nu-4 is ((2R,3S)-3-((butoxy(hydroxy)phosphoryl)oxy)tetrahydrofuran-2-yl) methyl butyl hydrogen phosphate. The molecular formula of Nu-4 is $C_{13}H_{28}O_9P_2$. Nu-4 has the following formula:

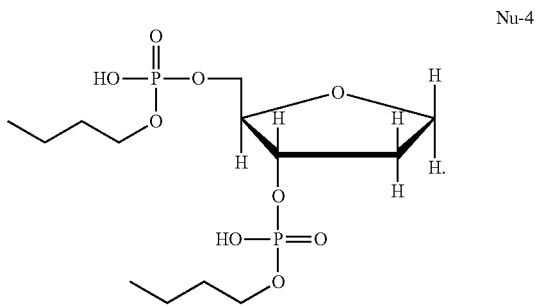

The chemical name of Nu-5 is Dibutyl (oxybis(ethane-2,1-diyl)) bis(hydrogen phosphate). The molecular formula of Nu-5 is $C_{12}H_{28}O_9P_2$. Nu-5 has the following formula:

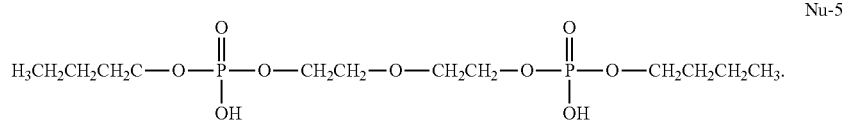

Nu-5

The chemical name of Nu-8 is ((2R,3S,5R)-5-(4-amino-2-oxopyrimidin-1(2H)-yl)-3-((butoxyoxidophosphor-yl)oxy)tetrahydrofuran-2-yl)methyl butyl phosphate. The molecular formula of Nu-8 is $C_{17}H_{29}N_3Na_2O_{10}P_2$. The molecular weight of Nu-8 is 543.11 Da. Nu-8 has the following formula:

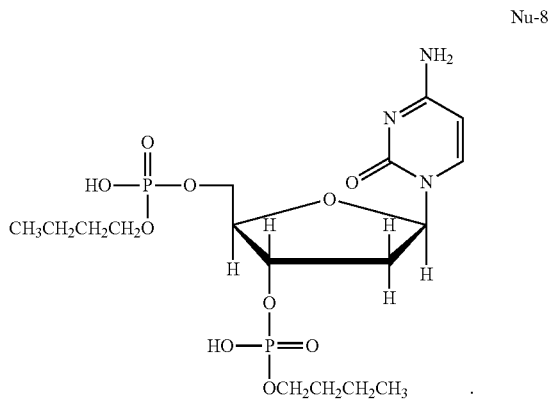

Nu-8

A compound of the present disclosure is described with reference to the specific compound illustrated herein. In addition, the compound of the present disclosure may exist in any number of different forms or derivatives, all within the scope of the present disclosure. Alternative forms or derivatives, include, for example, pharmaceutically acceptable salts, prodrugs and active metabolites, tautomers, and solid forms, including without limitation different crystal forms, polymorphic or amorphous solids, including hydrates and solvates thereof, and other forms.

Unless specified to the contrary, specification of the compound of the present disclosure herein includes pharmaceutically acceptable salts of such compound. Thus, the compound of the present disclosure can be in the form of pharmaceutically acceptable salts or can be formulated as pharmaceutically acceptable salts. Contemplated pharmaceutically acceptable salt forms of the present disclosure include, without limitation, mono, bis, tris, tetrakis, and so on. Pharmaceutically acceptable salts of the present disclosure are non-toxic in the amounts and concentrations at which such pharmaceutically acceptable salts are administered. The preparation of such pharmaceutically acceptable salts of the present disclosure can facilitate the pharmacological use by altering the physical characteristics of a compound of the present disclosure without preventing it from exerting its physiological effect.

As used herein, the term "pharmaceutically acceptable," with respect to salts and formulation components such as carriers, excipients, and diluents, refers to those salts and components which are not deleterious to a patient and which are compatible with other ingredients, active ingredients, salts or components. Pharmaceutically acceptable includes "veterinarily acceptable," and thus includes both human and non-human mammal applications independently.

As used herein, the term "pharmaceutically acceptable salt" refers to salts commonly used to form alkali metal salts and to form addition salts of free acids or free bases. Such salts include, for example, the pharmaceutically acceptable salts listed in Handbook of Pharmaceutical Salts, which are known to the skilled artisan. Salt formation can occur at one or more positions having labile protons. The pharmaceutically acceptable salts of a compound of the present disclosure include both acid addition salts and base addition salts.

In some embodiments, suitable pharmaceutically acceptable acid addition salts of the compounds of the present disclosure may be prepared from an inorganic acid or an organic acid. Examples of such inorganic acids include without limitation hydrochloric, hydrobromic, hydroiodic, nitric, carbonic, sulfuric, and phosphoric acid. Appropriate organic acids include without limitation aliphatic, cycloaliphatic, aromatic, arylaliphatic, heterocyclic, carboxylic, and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, beta-hydroxybutyric, malonic, galactic, and galacturonic acid, to name a few. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts, among others.

In some embodiments, suitable pharmaceutically acceptable base addition salts of the compounds of the present disclosure include without limitation metallic salts made from aluminum, calcium, lithium, magnesium, potassium, sodium and zinc, or organic salts made from N,N'-dibenzylethylene-diamine, chloroprocaine, choline, diethanolamine, ethylenediamine, N-methylglucamine, lysine, arginine, and procaine. All of these salts may be prepared by conventional means from a compound of the present disclosure by treating a compound of the present disclosure with the appropriate acid or base. Pharmaceutically acceptable basic/cationic salts also include diethanolamine, ammonium, ethanolamine, piperazine and triethanolamine salts, to name a few. In some embodiments, a pharmaceutically acceptable salt of the present disclosure comprises a monovalent cation or a divalent cation.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium ((2R,3S, 5R)-5-(4-amino-2-oxopyrimidin-1(2H)-yl)-3-((butoxyoxidophosphor-yl)oxy)tetrahydrofuran-2-yl)methyl butyl phosphate. In some embodiments, the calcium salt is calcium ((2R,3 S,5R)-5-(4-amino-2-oxopyrimidin-1(2H)-yl)-3-((butoxyoxidophosphor-yl)oxy)tetrahydrofuran-2-yl)methyl butyl phosphate. In some embodiments, the sodium salt is sodium ((2R,3S,5R)-5-(4-amino-2-oxopyrimidin-1(2H)-yl)-3-((butoxyoxidophosphor-yl)oxy)tetrahydrofuran-2-yl) methyl butyl phosphate. In some embodiments, the potassium salt is potassium ((2R,3S,5R)-5-(4-amino-2-oxopyrimidin-1(2H)-yl)-3-((butoxyoxidophosphor-yl)oxy) tetrahydrofuran-2-yl)methyl butyl phosphate. In some embodiments, the magnesium salt is magnesium ((2R,3S,5R)-5-(4-amino-2-oxopyrimidin-1(2H)-yl)-3-((butoxyoxidophosphor-yl)oxy)tetrahydrofuran-2-yl)methyl butyl phosphate. In some embodiments, the cobalt salt is cobalt ((2R,3 S,5R)-5-(4-amino-2-oxopyrimidin-1(2H)-yl)-3-((butoxyoxidophosphor-yl)oxy)tetrahydrofuran-2-yl)methyl butyl phosphate.

Pharmaceutically acceptable salts of the present disclosure can be prepared by standard techniques known in the art to which the present disclosure pertains. For example, the free-base form of a compound of the present disclosure can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, including, for example, treatment of the free acid with an appropriate inorganic or organic base.

In addition to the compound of the present disclosure, the present disclosure also includes prodrugs (e.g., pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Typically, the prodrug is inactive, or less active than the active compound, but may provide one or more advantageous handling, administration, and/or metabolic properties. Some prodrugs are activated enzymatically to yield the active compound or a compound may undergo further chemical reaction to yield the active compound. Prodrugs may proceed from prodrug form to active form in a single step or may have one or more intermediate forms which such forms have activity or may be inactive.

Prodrugs can be conceptually divided into two non-exclusive categories, including bioprecursor prodrugs and carrier prodrugs. Generally, bioprecursor prodrugs are compounds that are inactive or have low activity compared to the corresponding active drug compound that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, and the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Such carrier prodrugs are often advantageous for orally administered drugs. In some instances, the transport moiety provides targeted delivery of the drug. For example, the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity and can be further metabolized to provide an active metabolite.

Metabolites of a compound of the present disclosure may be identified using routine techniques known in the art, and their activities determined using tests such as those described in Bertolini et al.; Wermuth, supra.

It is understood by those skilled in the art that some compounds may exhibit tautomerism. In such cases, the formulae provided herein expressly depict only one of the possible tautomeric forms. It is therefore to be understood that the compound of the present disclosure intends to represent any tautomeric form of the depicted compound and is not to be limited merely to the specific tautomeric form depicted by the drawing of the compound.

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition (i.e., a free base or free acid of the compound of interest forms an acid/base reaction with a corresponding addition base or addition acid, respectively, resulting in an ionic charge interaction), co-crystals are a new chemical species that is formed between neutral compounds, resulting in the compound and an additional molecular species in the same crystal structure.

In some instances, the compound of the present disclosure is complexed with an acid or a base, including without limitation base addition salts such as, for example, ammonium, diethylamine, ethanolamine, ethylenediamine, diethanolamine, t-butylamine, piperazine, meglumine; acid addition salts, such as, for example, acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate, and tosylate; and amino acids such as, for example, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

Additionally, the compound of the present disclosure is intended to cover hydrated or solvated as well as unhydrated or unsolvated forms. Other examples of solvates include without limitation the compound of the present disclosure in combination with a suitable solvent, such as isopropanol, ethanol, methanol, DMSO, ethyl acetate, acetic acid or ethanolamine, and the like.

In some embodiments, a compound of the present disclosure is a protonated compound. As used herein, the term "protonated compound" refers to a compound of the present disclosure that is protonated by adding protons (or positively charged hydrogen ions) to proton acceptor sites of a compound of the present disclosure. In some embodiments, the proton acceptor sites include the phosphate groups of a compound of the present disclosure as well as any additional proton acceptor sites on either the ribose or the butyl groups of a compound of the present disclosure.

As the number of proton acceptor sites that are protonated on a compound of the present disclosure increases, the pH obtained when a compound of the present disclosure is dissolved in water having a pH of 7 decreases and thus the amount of protonation of a compound of the present disclosure can be determined by measuring the pH of solutions of water after addition of a compound of the present disclosure. pH indicates the hydrogen ion concentration of a solution. Solutions with a high concentration of hydrogen ions have a low pH and are therefore acidic, whereas solutions with a low concentration of hydrogen ions have a high pH and are therefore basic. In some embodiments, the compounds of the present disclosure are protonated so that when dissolved in water (pH 7) such compounds form an aqueous solution having a pH of from less than about pH 7 to about pH 1. As used herein, the term "about," when used with numerical values is to be read as including the amount(s) specified and variations of 20%, 10%, 5%, 1%, 0.5%, and 0.1% of the amount specified. In some embodiments, a compound of the present disclosure is a protonated compound having a pH when dissolved in water of from less than about pH 6 to about pH 1. In some embodiments, a compound of the present disclosure is a protonated compound having a pH when dissolved in water of from about pH 5 to about pH 1. In some embodiments, a compound of the present disclosure is a protonated compound having a pH when dissolved in water of from about pH 4.5 to about pH 1. In some embodiments, a compound of the present disclosure is a protonated compound having a pH when dissolved in water of from about pH 4 to about pH 1. In some embodiments, a compound of the present disclosure is a protonated compound having a pH when dissolved in water of from about pH 3 to about pH 1. In some embodiments, a compound of the present disclosure is a protonated compound having a pH when dissolved in water of from about pH 2 to about pH 1. In some embodiments, a compound of the present disclosure is a protonated compound having a pH when dissolved in water of about pH 3 to about pH 5. In some embodiments, a compound of the present disclosure is a protonated compound having a pH when dissolved in water of about pH 3 to about pH 4.

In some embodiments, protonation can be accomplished by incubating a compound of the present disclosure in the presence of a strong acid. Although a compound of the present disclosure can be protonated by adding protons to the reactive sites on the compound, other modifications of a compound of the present disclosure are possible and are intended to be encompassed by the term protonated compound as used herein. In some embodiments, protonated forms of the compounds of the present disclosure can be generated by subjecting the purified, partially purified or crude compounds to a low pH (e.g., acidic) environment. In some embodiments, purified or crude compounds can be protonated with acid, including phosphoric acid, nitric acid, hydrochloric acid, and acetic acid.

Other procedures to prepare a protonated compound of the present disclosure known to the skilled artisan are equally contemplated to be within the scope of the present disclosure. In some embodiments, once the compounds of the present disclosure have been protonated, such compounds may be separated from any undesired components such as, for example, excess acid.

The skilled artisan would know of many ways to separate the compounds from undesired components, including but not limited to using an H+-cation exchanger (e.g., H+-SCX). In some embodiments, the compounds of the present disclosure may be subjected to chromatography following protonation. In some embodiments, a compound of the present disclosure is run over a poly(styrene-divinyl benzene) based resin (e.g., Hamilton's PRP-1 or 3 and Polymer Lab's PLRP) following protonation.

In some embodiments, the protonated compounds of the present disclosure can be used directly. In some embodiments, the protonated compounds of the present disclosure can be processed further to remove any excess acid or salt, e.g., via precipitation, reverse phase chromatography, diafiltration or gel filtration. In some embodiments, the protonated compounds of the present disclosure can be concentrated by lyophilization, solvent evaporation, and the like. In some embodiments, when suspended in water or saline, the compounds of the present disclosure generally exhibit a pH of from about pH 3 to about pH 5 depending upon the level of protonation/acidification, which is determined by how much acid is used in the acidification process. In some embodiments, compounds of the present disclosure can be protonated by passage over a cation exchange column charged with hydrogen ions.

In some embodiments, utilization of two butyl groups in a compound of the present disclosure prevents or limits substantial nuclease degradation, including without limitation exonuclease degradation, of a compound of the present disclosure. In some embodiments, the butyl groups are positioned to protect the ribose of a compound of the present disclosure. Percent acid degradation may be determined using analytical HPLC to assess the loss of functional molecules or by other suitable methods. Acid degradation is generally measured as a function of time. In some embodiments, the compounds of the present disclosure are also nuclease resistant, which allows such compounds to maintain activity (e.g., pH stability) in an in vivo setting. Percent degradation of the compounds of the present disclosure in a setting containing a nuclease may be determined by methods known to those skilled in the art, such as, for example, mass spectroscopy. Nuclease degradation is generally measured as a function of time. In some embodiments, a reference compound is employed in determining the extent or rate of acid or nuclease degradation. In some embodiments, the compounds of the present disclosure are 10%, 20%, 30%, 40%, 50%, 70%, 90%, 100%, 150%, 200%, 300%, 500% or 750% more stable than a reference compound.

A compound of the present disclosure in accordance with some embodiments is useful as an antimicrobial having activity against any microbe. As used herein, the terms "microbe," "microbial," and like terms refers to bacteria, fungi, protozoa, viruses, yeast, and the like. As used herein, the term "antimicrobial" refers to a compound of the present disclosure having the ability to kill or inhibit the growth of a microbe, or to attenuate the severity of a microbial infection. A non-limiting list of the bacteria that a compound of the present disclosure is effective against include without limitation gram positive bacteria, gram negative bacteria, slow growing bacteria and acid fast bacteria, and any species included in the following genera: *Aerococcus, Listeria, Streptomyces, Chlamydia, Lactobacillus, Eubacterium, Burkholderia, Stentrophomonas, Achromobacter, Arachnid, Mycobacterium, Peptostreptococcus, Staphylococcus, Corynebacterium, Erysipelothrix, Dermatophilus, Rhodococcus, Pseudomonas, Streptococcus, Bacillus, Peptococcus, Pneumococcus, Micrococcus, Neisseria, Klebsiella, Kurthia, Nocardia, Serratia, Rothia, Escherichia, Propionibacterium, Actinomyces, Helicobacter, Enterococcus, Shigella, Vibrio, Clostridium, Salmonella, Yersinia,* and *Haemophilus.*

A non-limiting list of the fungi that a compound of the present disclosure is effective against include without limitation *Trichophyton, Epidermophyton, Microsporum, Candida albicans* and other *Candida* species, *Pityrosporum orbiculare, Trichophyton mentagrophytes, Trichophyton rubrum, Epidermophyton floccosurn,* and *Trichophyton tonsurans.* A non-limiting list of the viruses that a compound of the present disclosure is effective against include without limitation human immunodeficiency virus (HIV), herpes simplex virus (HSV), cytomegalovirus (CMV), Hepatitis B virus (HBV), Hepatitis C virus (HCV), and influenza virus.

The terms "treatment," "treating," and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease (or infection) and/or adverse effect attributable to the disease (or infection). The terms "treatment," "treating," and the like as used herein also include without limitation:

(a) preventing oral mucositis from occurring in a patient who may be predisposed to but has not yet been diagnosed as having it;

(b) reducing the risk that a patient will develop oral mucositis (for example, following radiation or chemotherapy treatment);

(c) inhibiting the progress or transmission of oral mucositis; or (d) relieving one or more of the symptoms of oral mucositis.

The terms "treatment," "treating," and the like also include preventing, inhibiting or relieving the symptoms of oral mucositis in a patient. The present disclosure is also directed toward treating patients with oral mucositis or predisposed to developing the disease, or ameliorating one or more symptoms of oral mucositis in a patent having the disease. As used herein, a "symptom" associated with oral mucositis includes any clinical or laboratory manifestation associated with the disease, and is not limited to what the subject can feel or observe. It will also be understood that "treatment" may include relieving the symptoms of oral mucositis in a patient in instances following a determination or diagnosis of oral mucositis in a patient.

As used herein, the term "patient" refers to a living organism that is treated with a compound of the present disclosure, including without limitation any mammal such as, for example, humans, other primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.).

In carrying out the methods of the present disclosure, an effective amount of a compound of the present disclosure is administered to a patient in need thereof. As used herein, the term "effective amount," in the context of administration, refers to the amount of a compound or pharmaceutical composition of the present disclosure that when administered to a patient is sufficient to prevent, alleviate or ameliorate one or more symptoms of a disease or condition (i.e., indication) and/or to prolong the survival of the patient being treated. Such an amount should result in no or few adverse events in the treated patient. Similarly, such an amount should result in no or few toxic effects in the treated patient. As those familiar with the art will understand, the amount of a compound or pharmaceutical composition of the present disclosure will vary depending upon a number of factors, including without limitation the activity of a compound of the present disclosure (in vitro, e.g. a compound of the present disclosure vs. target, or in vivo activity in animal efficacy models), pharmacokinetic results in animal models (e.g., biological half-life or bioavailability), the type of patient being treated, the patient's age, size, weight, and general physical condition, the disorder associated with the patient, and the dosing regimen being employed in the treatment.

In some embodiments of the present disclosure, an effective amount of a compound of the present disclosure to be delivered to a patient in need thereof can be quantified by determining micrograms of a compound of the present disclosure per kilogram of patient body weight. In some embodiments, the amount of a compound of the present disclosure administered to a patient is from about 0.1 to about 1000 milligram (mg) of a compound of the present disclosure per kilogram (kg) of patient body weight. In some embodiments, the amount of a compound of the present disclosure administered to a patient is from about 0.1 to about 500 mg of a compound of the present disclosure per kg of patient body weight. In some embodiments, the amount of a compound of the present disclosure administered to a patient is from about 0.1 to about 300 mg of a compound of the present disclosure per kg of patient body weight. In some embodiments, the amount of a compound of the present disclosure administered to a patient is from about 0.1 to about 200 mg of a compound of the present disclosure per kg of patient body weight. In some embodiments, the amount of a compound of the present disclosure administered to a patient is from about 0.1 to about 100 mg of a compound of the present disclosure per kg of patient body weight. As those of ordinary skill in the art understand multiple doses may be used.

The present disclosure also provides a pharmaceutical composition for treating oral mucositis. In some embodiments, the pharmaceutical composition comprises a Bisphosphocin, or a pharmaceutically acceptable salt thereof, and a pharmaceutically acceptable carrier. In some embodiments, the Bisphosphocin is selected from the group consisting of Nu-2, Nu-3, Nu-4, Nu-5, and Nu-8. As used herein, the term "pharmaceutical composition" refers to a pharmaceutical preparation that contains a compound of the present disclosure, or a pharmaceutically acceptable salt thereof, and is suitable for administration to a patient for therapeutic purposes. The terms "pharmaceutical composition" and "formulation" are used interchangeably herein.

In some embodiments, the pharmaceutical composition may include at least one pharmaceutically acceptable component to provide an improved formulation of a compound of the present disclosure, including without limitation one or more pharmaceutically acceptable carriers, excipients or diluents. The carrier, excipient or diluent may take a wide variety of forms depending on the form of preparation desired for administration.

As used herein, the term "carrier" includes without limitation calcium carbonate, calcium phosphate, various sugars, such as lactose, glucose, or sucrose, types of starch, cellulose derivatives, gelatin, lipids, liposomes, nanoparticles, pharmaceutically acceptable liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like.

As used herein, the term "excipient" generally includes without limitation fillers, binders, disintegrants, glidants, lubricants, complexing agents, solubilizers, stabilizer, preservatives, and surfactants, which may be chosen to facilitate administration of the compound by a particular route. Suitable excipients may also include, for example, colloidal silicon dioxide, silica gel, talc, magnesium silicate, calcium silicate, sodium aluminosilicate, magnesium tri silicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil, mineral oil, polyethylene glycol (e.g., PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g., 2-hydroxypropyl-delta-cyclodextrin), polysorbates (e.g., polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g., a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

As the skilled artisan understands, any diluent known in the art may be utilized in accordance with the present disclosure. In some embodiments of the present disclosure, the diluent is water soluble. In some embodiments of the present disclosure, the diluent is water insoluble. As used herein, the term "diluent" includes without limitation water, saline, phosphate buffered saline (PBS), dextrose, glycerol, ethanol, buffered sodium or ammonium acetate solution, or the like, and combinations thereof.

In some embodiments, the pharmaceutical composition is a human pharmaceutical composition. As used herein, the term "human pharmaceutical composition" refers to a pharmaceutical composition intended for administration to a human.

In some embodiments, the pharmaceutical compositions of the present disclosure are in the form of a mouthwash or in admixture with a gel-like vehicle. In some embodiments, the mouthwash generally comprises an aqueous mixture of diluents, soaps, flavorings, and/or colorants. In some embodiments, the mouthwash is combined with other antibacterial agents. In some embodiments, the gel-like vehicle generally comprises a mixture of a water-soluble gelling agent and a humectant, and may optionally contain other ingredients such as sweetening agents, and preservatives. In some embodiments, the mouthwash and the gel-like pharmaceutical composition provide superior mucoadhesion properties and residence time in the mouth and have favorable moistening and flavor properties that are associated with high patient compliance.

In some embodiments, the pharmaceutical compositions of the present disclosure comprise a diluent selected from the group consisting of water, glycerol, mannitol, saline, and phosphate buffered saline. In some embodiments, the diluent is water. In some embodiments, the water is present in the pharmaceutical composition in an amount from about 65% to about 97.5% (weight/weight).

In some embodiments, the pharmaceutical composition further comprises a saline diluent wherein a compound of the present disclosure is dissolved at a concentration in the range of from about 1 to about 20%, such as from about 1 to about 10%, and wherein the pH generally is in the range of from about 1.25 to about 5, such as at values of 1.5, 2, 3 and 4. In some embodiments, the pH may be adjusted by any pharmaceutically acceptable means, such as by addition of an effective amount of 10% HCl.

In some embodiments, mouthwash pharmaceutical compositions are non-sterile aqueous solutions used for deodorant, refreshing and/or antiseptic effect. In some embodiments, mouthwash pharmaceutical compositions contain alcohol as a preservative and a semi-active ingredient. In some embodiments, the amount of alcohol ranges from 18-26% and, in some embodiments, the remainder of the pharmaceutical composition is comprised primarily of water. In some embodiments, the mouthwash contains one or more Bisphosphocins present in an amount effective to treat or prevent oral mucositis.

In some embodiments, the gel and mouthwash pharmaceutical compositions disclosed herein are useful for treating infections caused by biofilms. Biofilms form when single microorganisms attach to a hydrated surface and grow as an adhesive cell matrix with other microorganisms. In some embodiments, the biofilms form densely packed communities of microbial cells which surround themselves with secreted polymers. In some embodiments, biofilms are notoriously difficult to treat and have been implicated in oral mucositis. Accordingly, some embodiments of the present disclosure include the treatment of infections caused by biofilms.

Some embodiments of the disclosure include a method for treating or preventing oral mucositis caused by biofilms comprising administering to the oral cavity of a patient in need thereof an effective amount of a mouthwash pharmaceutical composition comprising a Bisphosphocin or a pharmaceutically acceptable salt thereof, or any combination thereof; and dissolved at a concentration in the range of from about 1 to about 10% in a diluent selected from the group consisting of saline and phosphate buffered saline, and at a pH generally in the range of from about 1.25 to about 5, with further embodiments having a pH 1.5 to about pH 4, or in the range of about pH 3 to about pH 4.

In some embodiments, the Bisphosphocins and/or pharmaceutical compositions are suitable for administration to a patient by any suitable means, including without limitation those means used to administer conventional antimicrobials. The Bisphosphocins and/or pharmaceutical compositions of the present disclosure may be administered using any applicable route that would be considered by one of ordinary skill, including without limitation oral, intravenous ("IV") injection or infusion, subcutaneous ("SC"), intramuscular ("IM"), intradermal, transdermal, percutaneously, subdermal, topical, and mucosal. Such dosage forms should allow a Bisphosphocin to reach target cells. Other factors are well known in the art and include considerations such as toxicity and dosage forms that retard a Bisphosphocin from exerting its effects. Techniques and formulations generally may be found in Remington: The Science and Practice of Pharmacy, 21st edition, Lippincott, Williams and Wilkins, Philadelphia, Pa., 2005.

In some embodiments, a compound of the present disclosure and/or pharmaceutical composition is adapted for topical administration. As used herein, the term "topical administration" refers to administration of a compound of the present disclosure to the skin surface or mucous membrane of a patient so that a compound of the present disclosure passes through the skin layer or mucous membrane. Transdermal administration and transmucosal administration are also encompassed within the term topical administration. As used herein, the term "transdermal" refers to passage of a compound of the present disclosure across at least one skin layer or mucous membrane of a patient. As used herein, "transmucosal" refers to passage of a compound of the present disclosure across a mucous membrane of a patient.

Unless otherwise stated or implied, the terms "topical administration," "transdermal administration," and "transmucosal administration" are used interchangeably herein.

A variety of topical delivery systems for delivering bioactive compounds to microbes in an patient are well known in the art. Such systems include without limitation lotions, creams, gels, oils, ointments, solutions, suspensions, emulsions, and the like by choice of appropriate carriers in the art. In some embodiments, a compound of the present disclosure is administered in the form of a gel including a polyhydric alcohol. In some embodiments, a compound of the present disclosure is administered in the form of a mouthwash.

In some embodiments, suitable carriers include without limitation vegetable or mineral oils, white petrolatum (e.g., white soft paraffin), branched chain fats or oils, animal fats and high molecular weight alcohol (e.g., greater than C12). In some embodiments, carriers are selected such that a compound of the present disclosure is soluble. In some embodiments, emulsifiers, stabilizers, humectants, and antioxidants may also be included as well as agents imparting color or fragrance, if desired. In some embodiments, an organic solvent or co-solvent such as ethanol or propanol may be employed in the Bisphosphocins and/or pharmaceutical compositions of the present disclosure. In some embodiments, evaporation of the solvent leaves a residue on the treated surface to inhibit reinfection. In some embodiments, penetrants appropriate to the barrier to be permeated are used. Such penetrants are generally known in the art and include without limitation bile salts and fusidic acid derivatives. In some embodiments, detergents may be used to facilitate permeation. In some embodiments, creams for topical administration are formulated from a mixture of mineral oil, self-emulsifying beeswax, and water in which mixture a compound of the present disclosure, dissolved in a small amount of solvent (e.g., an oil), is admixed. In some embodiments, the specific topical delivery system used depends on the location of the microbes.

In some embodiments, other materials may also be added to the topical pharmaceutical compositions of the present disclosure have additional moisturizing effects and to improve the consistency of the pharmaceutical composition. Examples of such compounds include without limitation cetyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat. Nos. 5,153,230 and 4,421,769. If it is desirable for the pharmaceutical composition to have additional cleaning effects in some embodiments, chemicals such as sodium lauryl sulfate or a metal salt of a carboxylic acid may be added.

In some embodiments, a wide variety of nonvolatile emollients are useful in the pharmaceutical compositions of the present disclosure. Non-limiting examples of such nonvolatile emollients are listed in McCutcheon's. In some embodiments, the nonvolatile emollients include silicones, hydrocarbons, esters, and mixtures thereof. In some embodiments, the esters include esters of monofunctional and difunctional fatty acids that have been esterified with alcohols and polyols (i.e., alcohols having two or more hydroxyl groups). In some embodiments, long chain esters of long chain fatty acids are utilized in the pharmaceutical compositions of the present disclosure (i.e., C10-40 fatty acids esterified with C10-40 fatty alcohols). Non-limiting examples of esters useful in the pharmaceutical compositions of the present disclosure include without limitation those selected from the group consisting of diisopropyl adipate, isopropyl myristate, isopropyl palmitate, myristyl propionate, ethylene glycol distearate, 2-ethylhexyl palmitate, isodecyl neopentanoate, C12-15 alcohol benzoate, di-2-ethylhexyl maleate, ceryl palmitate, myristyl myristate, stearyl stearate, cetyl stearate, behenyl behenrate, and mixtures thereof.

Examples of silicone emollients useful in the pharmaceutical compositions of the present disclosure include without limitation polyalkylsiloxanes, cyclic polyalkylsiloxanes, and polyalkylarylsiloxanes. Suitable commercially available polyalkylsiloxanes include the polydimethylsiloxanes, which are also known as dimethicones, non-limiting examples of which include the Vicasil™ series sold by General Electric Company and the Dow Corning™ 200 series sold by Dow Corning Corporation. Commercially available polyalkylsiloxanes include cyclomethicones (Dow Corning™ 244 fluid), Dow Corning™ 344 fluid, Dow Corning™ 245 fluid and Dow Corning™ 345), among others. A suitable commercially available trimethylsiloxysilicate is sold as a mixture with dimethicone as Dow Corning™ 593 fluid. Also useful in the pharmaceutical compositions of the present disclosure are dimethiconols, which are hydroxyl terminated dimethyl silicones. Suitable commercially available dimethiconols are typically sold as mixtures with dimethicone or cyclomethicone (e.g., Dow Corning™ 1401, 1402, and 1403 fluids). Suitable commercially available polyalkylarylsiloxanes include SF1075 methylphenyl fluid (sold by General Electric Company) and 556 Cosmetic Grade phenyl trimethicone fluid (sold by Dow Coring Corporation).

Hydrocarbons suitable for use in the pharmaceutical compositions of the present disclosure include without limitation straight and branched chain hydrocarbons having from about 10 to about 30 carbon atoms. In some embodiments, the straight and branched chain hydrocarbons have from about 12 to about 24 carbon atoms. In some embodiments, the straight and branched chain hydrocarbons have from about 16 to about 22 carbon atoms. Non-limiting examples of such hydrocarbon materials include dodecane, squalane, cholesterol, 5 hydrogenated polyisobutylene, docosane (i.e., a C22 hydrocarbon), hexadecane, and isohexadecane (a commercially available hydrocarbon sold as Permethyl™ 101A by Presperse, South Plainsfield, N.J.), among others.

In some embodiments, the topical pharmaceutical compositions of the present disclosure include propylene glycol. In some embodiments, propylene glycol acts as a surfactant and assists in penetration, contact, and absorption of a compound of the present disclosure. In some embodiments, propylene glycol serves as a preservative. In some embodiments, the pharmaceutical compositions of the present disclosure include a non-ionic surfactant, such as, for example, polysorbate. Such a surfactant provides better surface contact of the pharmaceutical compositions of the present disclosure with mucosa by further reducing surface tension.

The topical pharmaceutical compositions of the present disclosure optionally may also be formulated with a lipophilic phase, such as, for example, emulsions and liposome dispersions. In some embodiments, liposomal formulations may extend circulation time of a compound of the present disclosure, increase permeability of a compound of the present disclosure, and improve overall efficacy of a compound of the present disclosure as an antimicrobial. In some embodiments, a compound of the present disclosure may be combined with a lipid, cationic lipid or anionic lipid. In some embodiments, the resulting emulsion or liposomal suspension in conjunction with the pH stabilizing qualities of a compound of the present disclosure can effectively increase the in vivo half-life of the activity of a pharmaceutical composition of the present disclosure. Examples of suitable anionic lipids for use with the pharmaceutical compositions of the present disclosure include, but are not limited to, cardiolipin, dimyristoyl, dipalmitoyl, dioleoyl phosphatidyl choline, phosphatidyl glycerol, palmitoyloleoyl phosphatidyl choline, phosphatidyl glycerol, phosphatidic acid, lysophosphatidic acid, phosphatidyl serine, phosphatidyl inositol, and anionic forms of cholesterol.

In some embodiments, a compound of the present disclosure is incorporated into liposomes. In some embodiments, neutral lipids, cholesterol, and/or polyethylene glycol (PEG) are utilized in such liposomes. In some embodiments, the liposomal composition is composed of partially hydrogenated soy phosphatidylcholine (PHSC), cholesterol, methoxy-terminated PEG (mPEG), and/or distearoyl phosphatidyl ethanolamine (DSPE). The liposomes can be prepared according to any suitable method known in the art.

In some embodiments, the Bisphosphicins and/or pharmaceutical compositions of the present disclosure are adapted for oral administration. As used herein, the term "oral administration" refers to administration of a compound of the present disclosure to the mouth of a patient for ingestion into the gastrointestinal tract. In some embodiments, the pharmaceutical compositions of the present disclosure can be formulated into conventional oral dosage forms including without limitation capsules, tablets, powders, and liquid preparations such as suspensions, solutions, elixirs, syrups, concentrated drops, and the like. In some embodiments, a compound of the present disclosure may be combined with solid excipients, optionally grinding a resulting mixture, and optionally processing the mixture of granules, after adding suitable auxiliaries, if desired, to obtain, for example, tablets, coated tablets, hard capsules, soft capsules, solutions (e.g., aqueous, alcoholic or oily solutions), and the like. In some embodiments, excipients suitable for use in the oral pharmaceutical compositions of the present disclosure include without limitation fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP or povidone); and oily excipients, including vegetable and animal oils, such as sunflower oil, olive oil, or cod liver oil. In some embodiments, the oral pharmaceutical compositions of the present disclosure may also contain disintegrating agents, such as, for example, cross-linked polyvinylpyrrolidone, agar, or alginic acid, or a salt thereof such as sodium alginate; a lubricant, such as talc or magnesium stearate; a plasticizer, such as glycerol or sorbitol; a sweetening agent such as sucrose, fructose, lactose, or aspartame; a natural or artificial flavoring agent, such as, for example, peppermint, oil of wintergreen, or cherry flavoring; or dye-stuffs or pigments, which may be used for identification or characterization of different doses or combinations. In some embodiments, the oral pharmaceutical compositions of the present disclosure may also contain dragée cores with suitable coatings. In some embodiments, concentrated sugar solutions may be used, which may optionally contain, for example, gum arabic, talc, poly-vinylpyrrolidone, carbopol gel, polyethylene glycol, titanium dioxide, lacquer solutions, and suitable organic solvents or solvent mixtures.

In some embodiments, the Bisphophocins and/or pharmaceutical compositions of the present disclosure that can be used orally include without limitation push-fit capsules made of gelatin ("gelcaps"), as well as soft, sealed capsules made of gelatin, and a plasticizer, such as glycerol or sorbitol. In some embodiments, the push-fit capsules can contain a compound of the present disclosure in admixture with filler such as lactose, binders such as starches, and/or lubricants such as talc or magnesium stearate and, optionally, stabilizers. In some embodiments including soft capsules, the active compound may be dissolved or suspended in suitable liquids, such as fatty oils, liquid paraffin, liquid polyethylene glycols, and the like.

In some embodiments, the Bisphosphocins and/or pharmaceutical compositions of the present disclosure are adapted for parenteral administration. As used herein, the term "parenteral administration" refers to a compound of the present disclosure being injected or infused into a patient and includes without limitation intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the pharmaceutical compositions of the present disclosure suitable for parenteral administration may be formulated in sterile liquid solutions, including without limitation physiologically compatible buffers or solutions, such as, for example, saline solution, Hank's solution or Ringer's solution. In some embodiments, the pharmaceutical compositions of the present disclosure suitable for parenteral administration may be prepared as dispersions in non-aqueous solutions, such as, for example, glycerol, propylene glycol, ethanol, liquid polyethylene glycols, triacetin, vegetable oils, and the like. In some embodiments, solutions may also contain a preservative, such as, for example, methylparaben, propylparaben, chlorobutanol, phenol, sorbic acid, thimerosal, and the like. In addition, pharmaceutical compositions of the present disclosure suitable for parenteral administration may be formulated in solid form, including, for example, lyophilized forms, and redissolved or suspended prior to use. In some embodiments, the pharmaceutical composition is administered via a needle.

In some embodiments of the present disclosure, a compound of the present disclosure and/or pharmaceutical composition is administered as a multiple dose regimen. As used herein, the term "multiple dose regimen" refers to a treatment time period of more than one day. In some embodiments of the present disclosure, the multiple dose regimen is a time period of up to about 2 days. In some embodiments of the present disclosure, the multiple dose regimen is a time period of up to about 3 days. In some embodiments of the present disclosure, the multiple dose regimen is a time period of up to about 4 days. In some embodiments of the present disclosure, the multiple dose regimen is a time period of up to about 5 days. In some embodiments of the present disclosure, the multiple dose regimen is a time period of up to about 6 days. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about one month. In some embodiments of the present disclosure, the multiple dose regimen is a time period of up to about two months. In some embodiments of the present disclosure, the multiple dose regimen is a time period of up to about three months. In some embodiments of the present disclosure, the multiple dose regimen is a time period of up to about four months. In some embodiments of the present disclosure, the multiple dose regimen is a time period of up to about five months. In some embodiments of the present disclosure, the multiple dose regimen is a time period of up to about six months. Other time periods may be used herein.

In some embodiments of the present disclosure, a compound of the present disclosure and/or pharmaceutical composition is administered as part of a chronic treatment regimen. As used herein, the term "chronic treatment regimen" refers to treatment with a compound of the present disclosure over an extended period of time during a patient's lifetime. In some embodiments, chronic treatment is lifelong treatment.

In some embodiments of the present disclosure, a compound of the present disclosure and/or pharmaceutical composition is administered as a single dose. In some embodiments of the present disclosure, a compound of the present disclosure is administered as a single unit dose. As used herein, the term "unit dose" is a predetermined amount of a compound of the present disclosure. The amount of a compound of the present disclosure is generally equal to the dosage of a compound of the present disclosure that would be administered to a patient or a convenient fraction of such a dosage such as, for example, one-half or one-third of such a dosage. According to the methods of the present disclosure, the terms "single dose" and "single unit dose" include embodiments wherein a compound of the present disclosure can be administered as a single application and administered as multiple applications.

In some embodiment, a compound of the present disclosure may also be used in combination with one or more additional active ingredients for treating the same disease or condition. As used herein, the term "active ingredient" refers to a therapeutically active compound, as well as any prodrugs thereof and pharmaceutically acceptable salts, hydrates, and solvates of the compound and the prodrugs. In some embodiments, such combination use includes administration of a compound of the present disclosure and one or more additional active ingredient at different times, or co-administration of a compound of the present disclosure and one or more additional active ingredients. In some embodiments, dosage may be modified for a compound of the present disclosure or one or more additional active ingredients used in combination, e.g., reduction in the amount dosed relative to a compound of the present disclosure or one or more additional active ingredients used alone, by methods well known to those of ordinary skill in the art. In some embodiments, co-administration includes simultaneous administration of a compound of the present disclosure and an additional active ingredient in the same dosage form, simultaneous administration of a compound of the present disclosure and an additional active ingredient in separate dosage forms, and separate administration of a compound of the present disclosure and an additional active ingredient. The amount of additional active ingredients to be given may be determined by one skilled in the art based upon therapy with a compound of the present disclosure. In some embodiments, a compound of the present disclosure may be co-formulated in the gel or mouthwash pharmaceutical composition described herein or co-administered with other active ingredients.

It is understood that use in combination includes use with one or more additional active ingredients or other medical procedure in which the one or more additional active ingredients or other medical procedure may be administered at different times (e.g., within a short time, such as within hours (e.g., 1, 2, 3, 4-24 hours, etc.), or within a longer time (e.g. 1-2 days, 2-4 days, 4-7 days, 1-4 weeks, etc.)) than a compound or pharmaceutical composition of the present disclosure, or at the same time as a compound or pharmaceutical composition of the present disclosure. Use in combination also includes use with one or more additional active ingredients or other medical procedure that is administered once or infrequently, such as surgery, along with a compound or pharmaceutical composition of the present disclosure administered within a short time or longer time before or after the administration of the one or more additional active ingredients or completion of the other medical procedure.

In some embodiments, the present disclosure provides for delivery of a compound or pharmaceutical composition of the present disclosure and one or more additional active ingredients delivered by a different route of administration or by the same route of administration. In some embodiments, the use in combination for any route of administration includes delivery of a compound or pharmaceutical composition of the present disclosure and one or more additional active ingredients delivered by the same route of administration together in any pharmaceutical composition, including pharmaceutical compositions in which the two compounds are chemically linked in such a way that such compounds maintain their therapeutic activity when administered. In some embodiments, the one or more additional active ingredients may be co-administered with a compound or pharmaceutical composition of the present disclosure. In some embodiments, use in combination by co-administration includes administration of co-formulations or formulations of chemically joined compounds, or administration of two or more compounds in separate formulations within a short time of each other (e.g., within an hour, 2 hours, 3 hours, up to 24 hours, etc.), administered by the same or different routes. In some embodiments, co-administration of separate formulations includes co-administration by delivery via one device, for example, the same inhalant device, the same syringe, etc., or administration from separate devices within a short time of each other. In some embodiments, co-formulations of a compound or pharmaceutical composition of the present disclosure and one or more additional active ingredients delivered by the same route includes preparation of the materials together such that they can be administered by one device, including the separate compounds combined in one formulation, or compounds that are modified such that the compounds are chemically joined, yet still maintain their biological activity. In some embodiments, such chemically joined compounds may have a linkage that is substantially maintained in vivo, or the linkage may break down in vivo, separating the two active components.

The present disclosure also provides a kit. In some embodiments, the kit comprises a compound according to the present disclosure, or a pharmaceutically acceptable salt thereof, or a pharmaceutical composition according to the present disclosure. As used herein, the term "kit" refers to any manufacture, such as, for example, a package, container, and the like, containing a compound according to the present disclosure, or a pharmaceutically acceptable salt thereof, or a pharmaceutical composition according to the present disclosure. In some embodiments, a compound according to the present disclosure, or a pharmaceutically acceptable salt thereof, or a pharmaceutical composition according to the present disclosure is packaged in a vial, bottle, tube, flask or patch, which may be further packaged within a box, envelope, bag, or the like. In some embodiments, a compound according to the present disclosure, or a pharmaceutically acceptable salt thereof, or a pharmaceutical composition according to the present disclosure is approved by the U.S. Food and Drug Administration or similar regulatory agency in the U.S. or a jurisdiction or territory outside the U.S. for administration to a patient. In some embodiments, the kit includes written instructions for use and/or other indication that a compound according to the present disclosure, or a pharmaceutically acceptable salt thereof, or a pharmaceutical composition according to the present disclosure is suitable or approved for administration to a patient. In some embodiments, a compound or composition of the present disclosure is packaged in unit dose or single unit dose form, such as, for example, single unit dose pills, capsules or the like. In some embodiments, the kit includes a dispenser.

The present disclosure also provides the use of a compound of the present disclosure, or a pharmaceutically acceptable salt thereof, for the manufacture of a medicament. As used herein, the term "medicament" refers to a pharmaceutical composition according to the present disclosure. In some embodiments, the medicament is for treating oral mucositis. In some embodiments, the pharmaceutical composition is contained in any manufacture, such as, for example, a package, container, and the like.

EXAMPLES

Examples related to the present disclosure are described below. In most cases, alternative techniques can be used. The examples are intended to be illustrative and are not limiting or restrictive of the scope of the invention as set forth in the claims.

Example 1

The compounds of the present disclosure are synthesized according to methods known to those of ordinary skill in the art. The methods described in U.S. Pat. Nos. 6,627,215; 6,211,162; 7,868,162; 7,176,191; 8,435,960; and 6,211,349; and U.S. Patent Application Publication Numbers 2017-0191062; 2018-0258128; and 2018-0353529, all of which are hereby incorporated by reference in their entireties, are well suited for synthesizing the compounds of the present disclosure.

Example 2

Nu-8 is synthesized according to the following method:

Synthesis of Nu-8

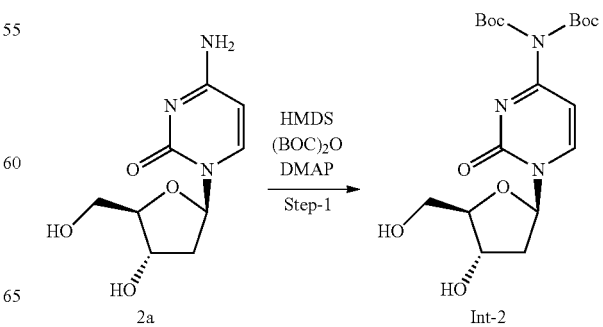

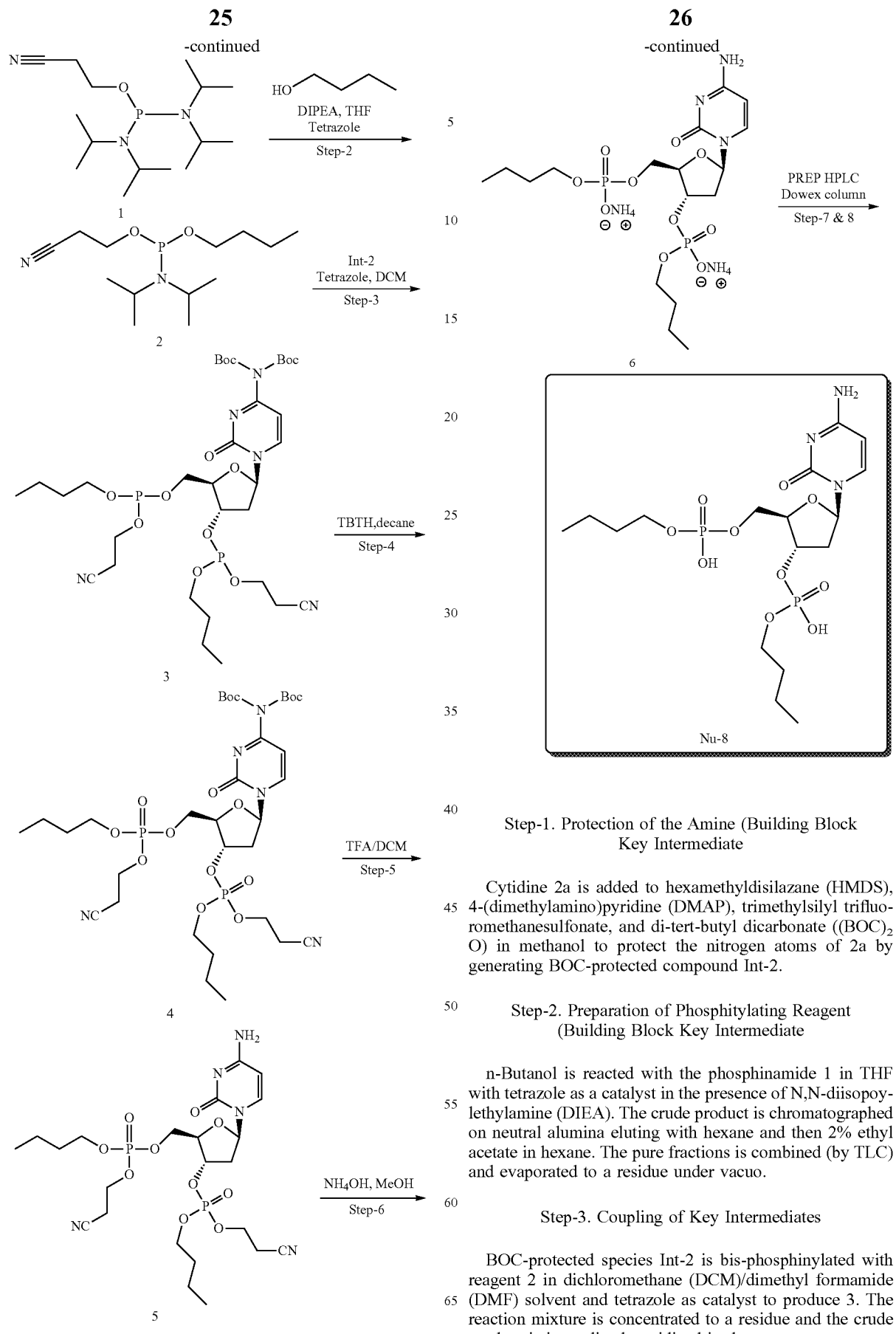

Step-1. Protection of the Amine (Building Block Key Intermediate

Cytidine 2a is added to hexamethyldisilazane (HMDS), 4-(dimethylamino)pyridine (DMAP), trimethylsilyl trifluoromethanesulfonate, and di-tert-butyl dicarbonate ((BOC)₂O) in methanol to protect the nitrogen atoms of 2a by generating BOC-protected compound Int-2.

Step-2. Preparation of Phosphitylating Reagent (Building Block Key Intermediate n-Butanol is reacted with the phosphinamide 1 in THF with tetrazole as a catalyst in the presence of N,N-diisopoylethylamine (DIEA). The crude product is chromatographed on neutral alumina eluting with hexane and then 2% ethyl acetate in hexane. The pure fractions is combined (by TLC) and evaporated to a residue under vacuo.

Step-3. Coupling of Key Intermediates

BOC-protected species Int-2 is bis-phosphinylated with reagent 2 in dichloromethane (DCM)/dimethyl formamide (DMF) solvent and tetrazole as catalyst to produce 3. The reaction mixture is concentrated to a residue and the crude product is immediately oxidized in the next step.

Steps 4 & 5. Oxidation and Amino Deprotection

The crude product 3 is oxidized with tert-butylhydroperoxide (TBTH) in the presence of decane to generate the bis-phosphonate species 4. Removal of the BOC groups is carried in DCM in the presence of trifluoroacetic acid (TFA) to yield 5. The crude product is chromatographed on silica gel eluting with ethyl acetate. The pure fractions (by TLC) are combined and evaporated to a residue under vacuo.

Step-6. Deprotection of the Phosphodiester

Hydrolysis of 5 with methanolic ammonium hydroxide (NH$_4$OH, MeOH) gives crude (I) ammonium salt (6).

Steps 7 & 8. Purification

Purification by preparative HPLC of 6 and conversion to the free acid with Dowex 50WX8-200 resin is carried out. Evaporation of the aqueous eluate provides (I) that is diluted with purified water to provide a 20% solution at its ambient pH.

Synthesis of Nu-8 Sodium Salt

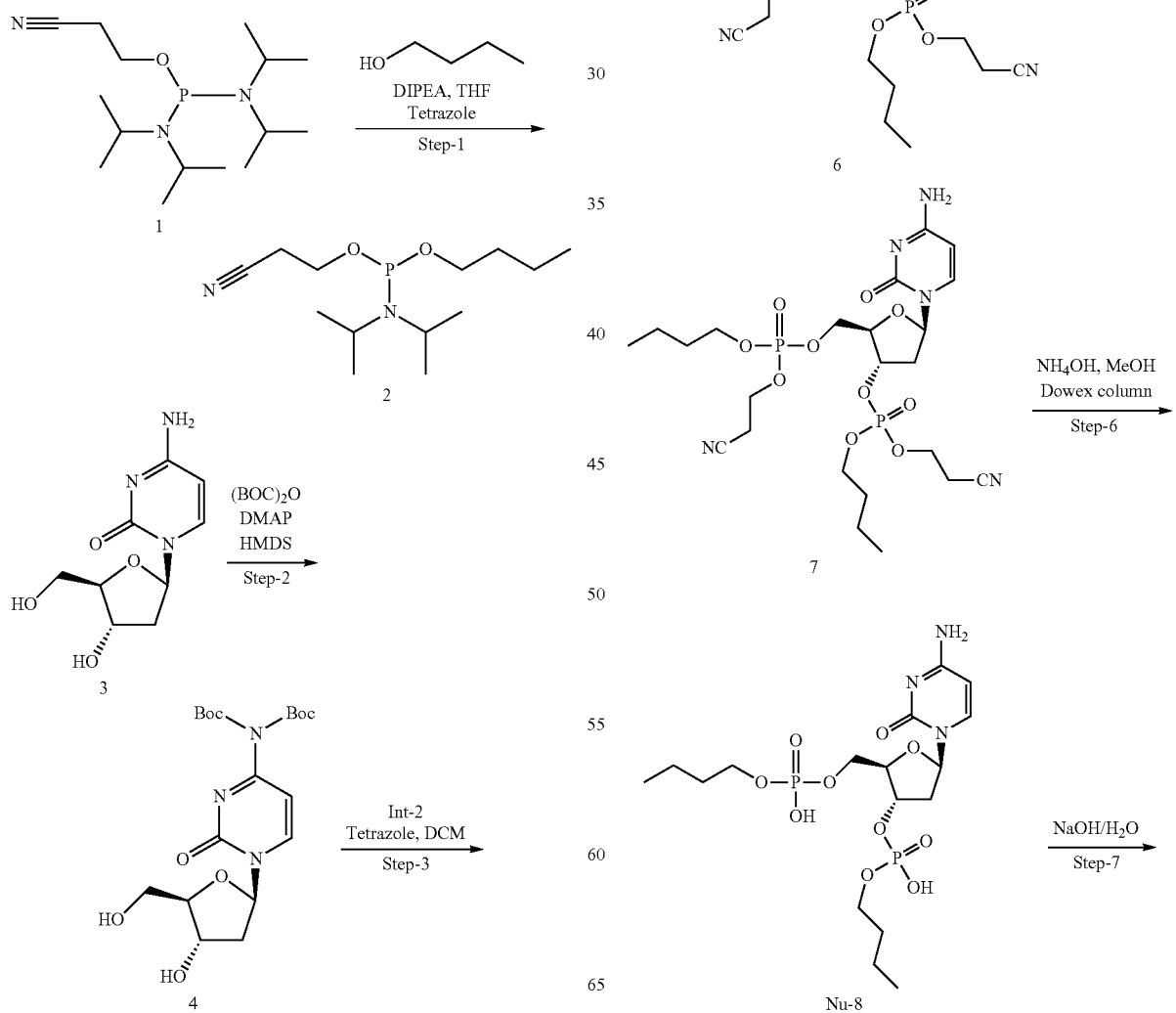

-continued

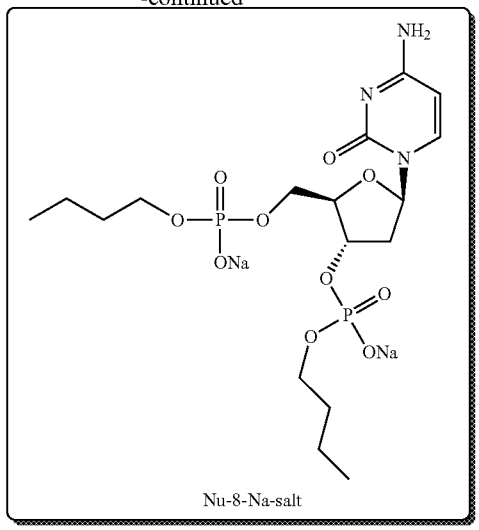

Nu-8-Na-salt

Synthesis of Compound-2

To a solution of compound-1 (1.0 kg, 3.3222 mol) in THF (6 L) is added DIEA (1.370 mL, 8.3055 mol) and tetrazole (230 g, 3.3222 mol) followed by n-butanol (275 mL, 2.99 mol) in THF (6 L) is added drop wise at 0° C. for 12 h. The reaction mixture is stirred at room temperature for 24 h. The progress of the reaction is monitored by TLC and after completion of the reaction, solid is filtered off. Filtrate is evaporated under reduced pressure at 40° C. to afford crude compound. Crude compound is dissolved in ethyl acetate (5 L). Organic layer is washed with water (3 L) and brine (2 L). Organic layer is dried over anhydrous $Na_2SO_4$ filtered and the solvent is evaporated under reduced pressure to obtain crude compound. The crude compound is purified by column chromatography over basic lumina ($Al_2O_3$), Compound eluted with 0-2% EtOAc in petroleum ether to afford Compound-2. (700 g, 76.92%) as pale yellow liquid. H-NMR (400 MHz, chloroform-d) δ 4.18-4.07 (m, 1H), 4.02 (q, J=6.6 Hz, 1H), 3.93-3.74 (m, 4H), 2.65 (td, J=6.5, 3.6 Hz, 2H), 1.31-1.23 (m, 4H), 1.18 (dd, J=6.8, 3.8 Hz, 12H), 0.93 (td, J=7.4, 3.1 Hz, 3H). LC-MS: 275 (M+H).

Synthesis of Compound-4

To solution of compound-3 (300 g, 1.321 mol) in hexamethyldisilazane (638 g, 3.964 mol) is added DMAP (16.11 g, 0.132 mol) followed by TMSOTf (7.22 g, 0.039 mol) is added at 0° C. and the resulting reaction mixture is stirred for 1 h at room temperature. After complete of starting material Boc-anhydride (1.4 L, 6.605 mol) is added at 0° C. for 1 h and the reaction mixture is stirred for 16 h at room temperature. To the reaction is added methanol (3 L) followed by triethylamine (1.5 L) at 0° C. for 1 h and the reaction mixture is stirred for 20 h at room temperature. Reaction mixture is concentrated under reduced pressure to get crude compound. Crude compound is diluted with ethyl acetate (3 L) and washed with water (1.0 L) and brine (1.0 L) solution; organic layer is dried over anhydrous $Na_2SO_4$, filtered and the solvent is evaporated under reduced pressure to get afford crude compound. The crude compound is purified by column chromatography silica gel (100-200 mesh) compound eluted 0-3% MeOH in DCM to afford Compound-4 (180 g, 31.89%) as off white solid. H-NMR (300 MHz, DMSO-d6) δ 8.41 (d, J=7.5 Hz, 1H), 6.84 (d, J=7.5 Hz, 1H), 6.06 (t, J=6.2 Hz, 1H), 5.28 (d, J=4.3 Hz, 1H), 5.07 (q, J=4.6, 4.0 Hz, 1H), 4.21 (q, J=4.1 Hz, 1H), 3.87 (q, J=3.7 Hz, 1H), 3.71-3.49 (m, 2H), 2.32 (m, 1H), 2.03 (dt, J=13.0, 6.2 Hz, 1H), 1.49 (s, 18H). LC-MS: 275 (M+H).

Synthesis of Compound-6

To a stirred solution of compound-4 (180 g, 0.421 mol) in THF (1.0 L) is added DIEA (348 mL, 2.105 mol) and tetrazole (176 g, 2.526 mol) at 0° C. To the resulting reaction mixture is added a solution of compound-2 (519 g, 1.896 mol) in THF (800 mL) drop wise at 0° C. for 1 h. The reaction mixture is stirred at room temperature for 16 h. After completion of the reaction, tert-butyl peroxide in decane (505 mL, 5 M) is added drop wise at 0° C. and the reaction mixture is stirred for 6 h at room temperature. The reaction is monitored by TLC. After completion of the reaction, the reaction mixture is concentrated at 40° C. and diluted with ethyl acetate (3 L) and washed with water (1 L) and brine (1 L) solution. Organic layer is dried over anhydrous $Na_2SO_4$ filtered and the solvent is evaporated under reduced pressure to get afford crude compound (350 g crude). The crude compound is purified by column chromatography through silica gel (100-200 mesh) column eluted with 0-5% MeOH in DCM. All collected pure fractions are concentrated to afford pure Compound-6 (220 g, 64.83%) as a wine red liquid. H-NMR (300 MHz, DMSO-$d_6$) δ 8.19 (dd, J=7.6, 1.3 Hz, 1H), 6.88 (d, J=7.5 Hz, 1H), 6.13 (t, J=10.5 Hz, 1H), 4.99 (s, 1H), 4.44 (s, 1H), 4.26-3.96 (m, 10H), 3.00-2.84 (m, 4H), 2.57-2.79 (m, 2H), 1.70-1.54 (m, 4H), 1.50 (s, 18H), 1.35 (m, 4H), 0.88 (qd, J=7.5, 2.5 Hz, 6H); LC-MS: 806 (M+H).

Synthesis of Compound-7

To a solution of Compound-6 (220 g, 0.273 mol) in DCM (4.4 L) is added TFA (210 mL, 2.732 mol) dropwise at 0° C. The reaction mixture is stirred at room temperature for 24 h. The reaction is monitored by TLC. After completion of the reaction, solvent is evaporated under reduced pressure to afford crude compound. The crude compound is purified by column chromatography silica gel (230-400 mesh). Compound eluted with 0-10% MeOH in DCM. All collected pure fractions are concentrated to afford pure Compound-7 (170 g, 84.67%) as a pale yellow liquid. H-NMR (300 MHz, DMSO-$d_6$) δ 7.61 (d, J=7.5 Hz, 1H), 7.27 (d, J=13.9 Hz, 2H), 6.19 (t, J=6.9 Hz, 1H), 5.74 (d, J=7.4 Hz, 1H), 4.96 (s, 1H), 4.10-3.93 (m, 11H), 2.93 (q, J=6.2 Hz, 4H), 2.29 (d, J=13.1 Hz, 2H), 1.61 (h, J=7.1 Hz, 4H), 1.35 (p, J=7.3 Hz, 4H), 0.89 (dq, J=7.9, 4.2 Hz, 6H); LC-MS: 606 (M+H).

Synthesis of Nu-8

To a stirred solution of Compound-7 (720 g, 1.1900 mol) in MeOH (5.0 L) is added aq. ammonia (600 mL) at 0° C. The reaction mixture is stirred at room temperature for 4 h. The reaction is monitored by TLC. After completion of the reaction, evaporate the MeOH under reduced pressure the aqueous layer is washed with DCM (1.5 L). The aqueous layer is passed through Dowex-$H^+$ resin. The water is removed under reduced pressure to afford Nu-8 (260 g, 43.84%) as an off white solid. H-NMR (300 MHz, DMSO-$d_6$) δ 8.94 (s, 1H), 8.49 (s, 1H), 7.97 (d, J=7.8 Hz, 1H), 6.08 (t, J=6.1 Hz, 1H), 5.95 (d, J=7.7 Hz, 1H), 4.76 (q, J=5.8 Hz, 1H), 4.15 (q, J=4.1 Hz, 1H), 4.08 (s, 1H), 3.83 (m, 6H), 2.43

(t, J=5.6 Hz, 2H), 1.67-1.44 (m, 4H), 1.44-1.26 (m, 4H), 0.95-0.82 (m, 6H), LC-MS: 500.15 (M+H).

Synthesis of Nu-8 Sodium Salt

To a stirred solution of compound-Nu-8 (260 g, 0.478 mol) in water (2.6 L), 1 N NaOH (950 mL) is added dropwise at 0° C. The reaction mixture is stirred at room temperature for 2 h. The reaction is monitored by TLC. After completion of the reaction, aqueous layer is washed with DCM (1.5 L). The aqueous layer is evaporated under reduced pressure to afford Nu-8 sodium salt (265 g, 93%) as off white solid. H-NMR (300 MHz, DMSO-$d_6$) δ 7.81 (d, J=7.2 Hz, 1H), 7.2 (bs, 1H), 7.0 (bs, 1H), 6.16 (t, J=4 Hz, 1H), 5.71 (d, J=7.6 Hz, 1H), 4.69 (bs, 1H), 3.75 (m, 1H), 3.71 (m, 1H), 3.8 (m, 4H), 2.2 (q, 1H), 1.89-1.96-1.44 (m, 1H), 1.49-1.39 (m, 4H), 1.34-1.23 (m, 4H), 0.88-0.84 (m, 6H).

Example 3

A Study of Nu-8 for the Treatment of Oral Mucositis Induced by Acute Radiation in Hamsters The objective of the study was to test the efficacy of Nu-8 in the treatment of oral mucositis induced by acute radiation in hamsters.

Location of Study Performance

The study was performed at Biomodels' AAALAC facility in Watertown, Mass. The in-life portion of this study was conducted from Aug. 13, 2019 to Sep. 11, 2019. Approval for this study (approval number 19-0611-1) was obtained from Biomodels IACUC. The Office of Laboratory Animal Welfare (OLAW) assurance number was A4591-01.

Animals

Normal male Syrian Golden Hamsters (Charles River Laboratories), aged 5 to 6 weeks, with average body weight (±SD) of 92.83±3.36 g at study commencement, were used. Animals were individually numbered using an ear punch and housed in small groups. Animals were acclimatized prior to study commencement. During this period, the animals were observed daily in order to reject animals that were in poor condition.

Housing

The study was performed in animal rooms provided with filtered air at a temperature of 70±5° F. and 50±20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity were recorded during the study, and the records retained.

Diet

Animals were fed with a Purina Labdiet® 5053 sterile rodent chow. Food and sterile water were provided ad libitum.

Animal Randomization and Allocations

Animals were randomly and prospectively divided into three (3) groups of eight (8) animals each prior to irradiation. Each animal was identified by an ear punch corresponding to an individual number. A cage card was used to identify each cage or label marked with the study number (LKW-01), treatment group number and animal numbers.

Test Article/Vehicle Preparation and Dosing

| | Test Articles and Vehicle Test Articles |
|---|---|
| Identity and Lot Number: | Nu-8 (lot # LWA-03-14) |
| Physical Description: | Dry Powder |
| Source: | Lakewood Amedex, Inc. |
| Vehicle: | 0.9% Normal Saline |
| Route of Administration: | Topical (directed to left cheek pouch) |
| Dosing Details: | 0.2 mL/dose - Dose Concentration (Low) = 1% Dose Concentration (High) = 10% |

Formulation:
1. Make fresh daily. Weigh out necessary amount of compound and dissolve in normal saline. Titrate with citric acid to bring pH of solution down to approximate 3.5 (pH range 3 to 4).
2. The vehicle administered to animals in Group 1 was also titrated with citric acid to a pH of ~3.5 (pH range 3 to 4).

Administration of Test Article

Route and Method of Application: Topical

Justification for Route of Administration: This route of administration has been used to demonstrate efficacy for a wide range of experimental compounds.

Frequency and Duration of Dosing: TID—Days -1 to 28

Administered Doses: Low=1%
    High=10%

Mucositis Induction

Mucositis was induced using a single of radiation (40 Gy) administered on Day 0. Radiation was generated with a 160-kilovolt potential (18.75-ma) source at a focal distance of 10 cm, hardened with a 3.0 mm Al filtration system. Irradiation targeted the left buccal pouch mucosa at a rate of 2-2.5 Gy/minute. Prior to irradiation, animals were anesthetized with an intraperitoneal injection of ketamine (160 mg/kg) and xylazine (8 mg/kg). The left buccal pouch was everted, fixed and isolated using a lead shield.

Mucositis Scoring

Starting on Day 6 and continuing every second day thereafter (Days 8, 10, 12, 14, 16, 18, 20, 22, 24, 26, 28) each animal was photographed and evaluated for mucositis scoring. For the evaluation of mucositis, the animals were anesthetized with an inhalation anesthetic and the left pouch everted. Mucositis was scored visually by comparison to a validated photographic scale (FIGS. 1A-1F), ranging from 0 for normal, to 5 for severe ulceration (clinical scoring). In descriptive terms, this scale is defined as follows:

TABLE 1

Mucositis Scoring

| Score | Description |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray color due to pseudomembrane. Cumulative size of ulcers should equal less than or equal to ¼ of the pouch. Severe erythema and vasodilation. |

TABLE 1-continued

Mucositis Scoring

| Score | Description |
|---|---|
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

A score of 1-2 is considered to represent a mild stage of the disease, whereas a score of 3-5 is considered to indicate moderate to severe ulcerative mucositis. Following visual clinical scoring, a photograph was taken of each animal's mucosa using a standardized technique. At the conclusion of the experiment, the photographs were randomly numbered and scored by two independent, trained observers who graded the images in blinded fashion using the above-described scale (blinded scoring). For each photograph, the actual blinded score was based on the average of the 2 observers' scores. Only the scores from the blinded, photographic evaluation were reported and used for statistical analyses. Hamsters reaching a mucositis severity score of 4 or higher received buprenorphine (0.5 mg/kg) SC twice a day for 48 hours or until score dropped below 4.

Statistical Analyses

Using the blinded photographs, statistical differences between treatment groups were determined using Mann-Whitney Rank Sum test and chi-square analysis with a critical value of 0.05. It was anticipated that up to 10% animal death may occur, primarily as a result of the administration of anesthetics. However, the number of animals expected to remain alive at Day 28 (6 per treatment group) was considered acceptable for statistical evaluation.

The difference in the number of days hamsters in each group have severe mucositis (score ≥3) was analyzed. On each day the animals were scored (evaluation day), the number of animals with a blinded mucositis score of ≥3 in each treatment group was compared to the Vehicle control group. Differences were analyzed on a daily as well as a cumulative basis. Treatment success was determined by a statistically significant lower number of hamsters with this score in a drug treatment group, versus Vehicle control as determined by chi-square analysis.

The rank sum differences in daily mucositis scores in treatment groups versus the Vehicle control group were determined. For each evaluation day the scores of the Vehicle control group were compared to that of the treated groups using the non-parametric rank sum analysis. Treatment success was determined by a statistically significant lowering of scores in the treated group on 2 or more days from Day 6 to Day 28.

To determine the effect of test articles on mucositis resolution, the time to healing was compared between the treatment and control groups. Resolution was defined as the absence of ulcerative lesions (mucositis scores <3).

Study Design

Twenty-four (24) male Syrian Golden Hamsters were used in the study. Mucositis was induced by an acute radiation dose of 40 Gy directed to their left buccal cheek pouch on Day 0 at a rate of 2-2.5 Gy/min. This was accomplished by anesthetizing the animals and everting the left buccal pouch, while protecting the rest of the animal's bodies with a lead shield. Mucositis was evaluated clinically starting on Day 6 and continuing on alternate days until Day 28. Hamsters reaching a mucositis severity score of 4 or higher received buprenorphine 0.5 mg/kg SC twice a day for 48 hours or until score drops below 4.

Test article or vehicle was given by topical application, directed to the left cheek pouch, TID from Days −1 to 28, as detailed in Table 2. On Day 0, dosing was performed 1-2 hrs PRIOR to irradiation.

On Day 28, all animals were euthanized via $CO_2$ inhalation and death was confirmed by monitoring heartbeat in accordance with USDA guidelines. No terminal collections were performed. The details of the study design are shown in Table 2.

TABLE 2

Study Design

| Group Number | Number of Animals | Radiation (Day 0) | Treatment | Dose Schedule* | Mucositis Evaluation |
|---|---|---|---|---|---|
| 1 | 8 Males | 40 Gy | Vehicle 0.2 mL/Dose (Topical) | TID Days 1-28 | Day 6-28 |
| 2 | 8 Males | 40 Gy | Compound 1 0.2 mL/Dose Low Dose (Topical) | TID Days 1 to 28 | Day 6-28 |
| 3 | 8 Males | 40 Gy | Compound 1 0.2 mL/Dose High Dose (Topical) | TID Days 1 to 28 | Day 6-28 |

*On Day 0, animals were dosed 1-2 hours PRIOR to irradiation.

Results and Discussion

Survival

There was one (1) unanticipated animal death during the study; animal #22 from Group 3 was sacrificed due to incomplete irradiation on Day 0.

Weight Change

Figure 2:
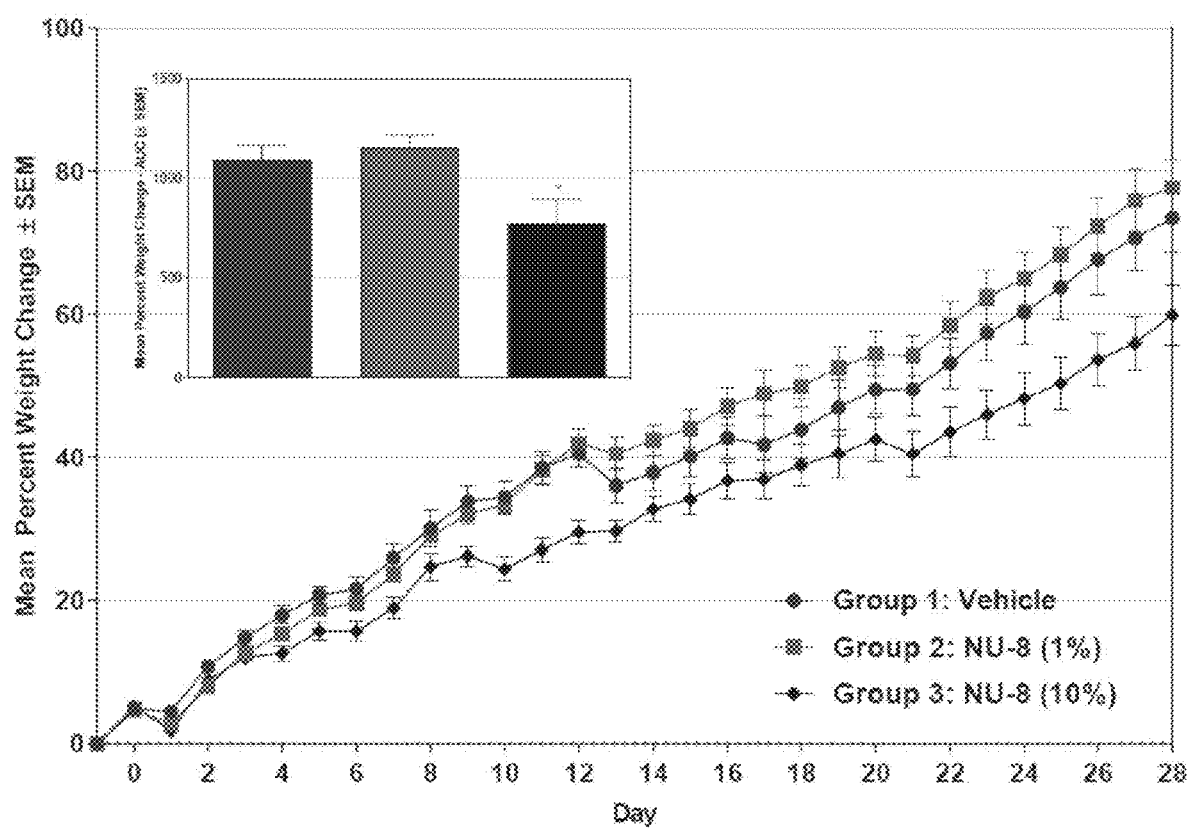
FIG. 2 shows mean daily percent weight change data for animals.

The mean daily percent body weight change data are shown in FIG. 2 for animals in all groups. Animals steadily gained weight throughout the duration of the study. In comparison to the vehicle group, animals in Group 3 exhibited statistically significant lower mean percent weight change ($p<0.05$) as determined by using Area-Under-the-Curve (AUC) analysis followed by evaluation with one-way ANOVA with Holm-Sidak's multiple comparisons post-hoc test.

Mucositis

Figure 3:
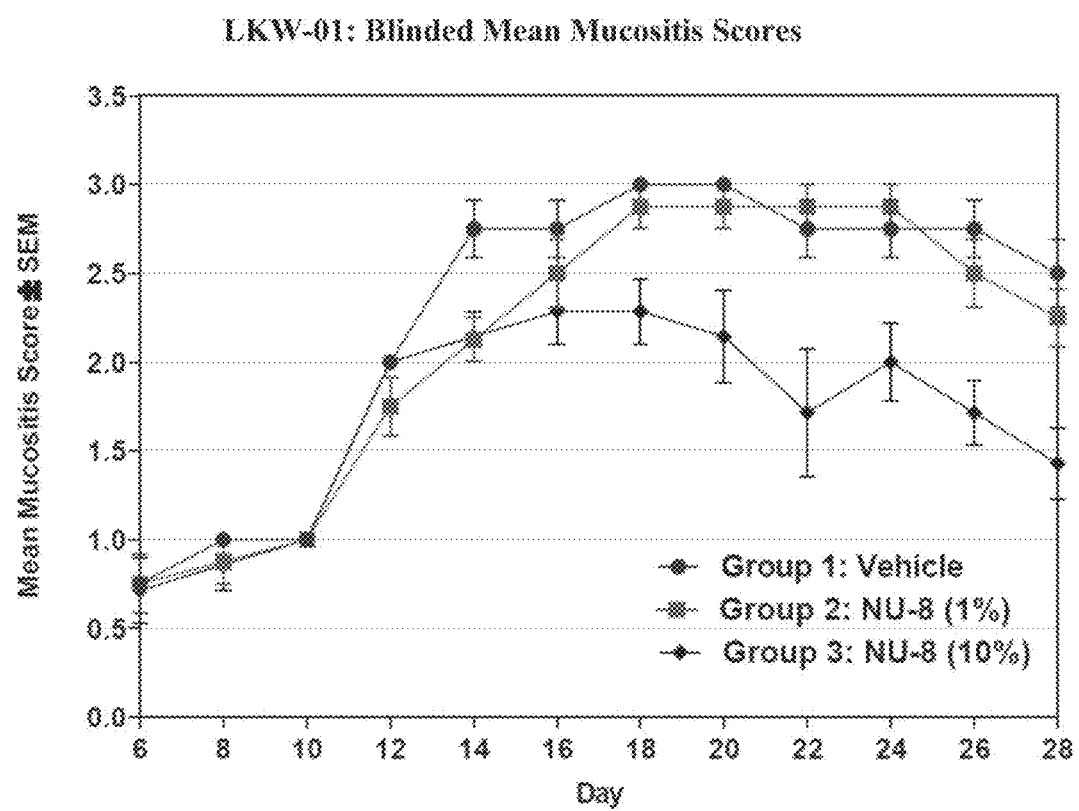
FIG. 3 shows mean daily mucositis scores for animals.

Mean daily mucositis scores are shown in FIG. 3. The maximum mean mucositis score observed in the Vehicle group was 3.00±0.00 and was first observed on Day 18. Animals dosed TID with 1% Nu-8 (Group 2) experienced peak mean mucositis scores of 2.88±0.13 on Day 18. Animals dosed TID with 10% Nu-8 (Group 3) experienced peak mean mucositis scores of 2.29±0.18 on Days 16 & 18. There was modest attenuation of disease onset exhibited by animals in both groups treated with Nu-8, but more so with in animals dosed with 10% concentration (Group 3). Indeed, a robust mitigation of disease severity was exhibited by animals dosed with 10% Nu-8 in comparison to vehicle-dosed animals.

Duration of Ulcerative Mucositis

Figure 4:
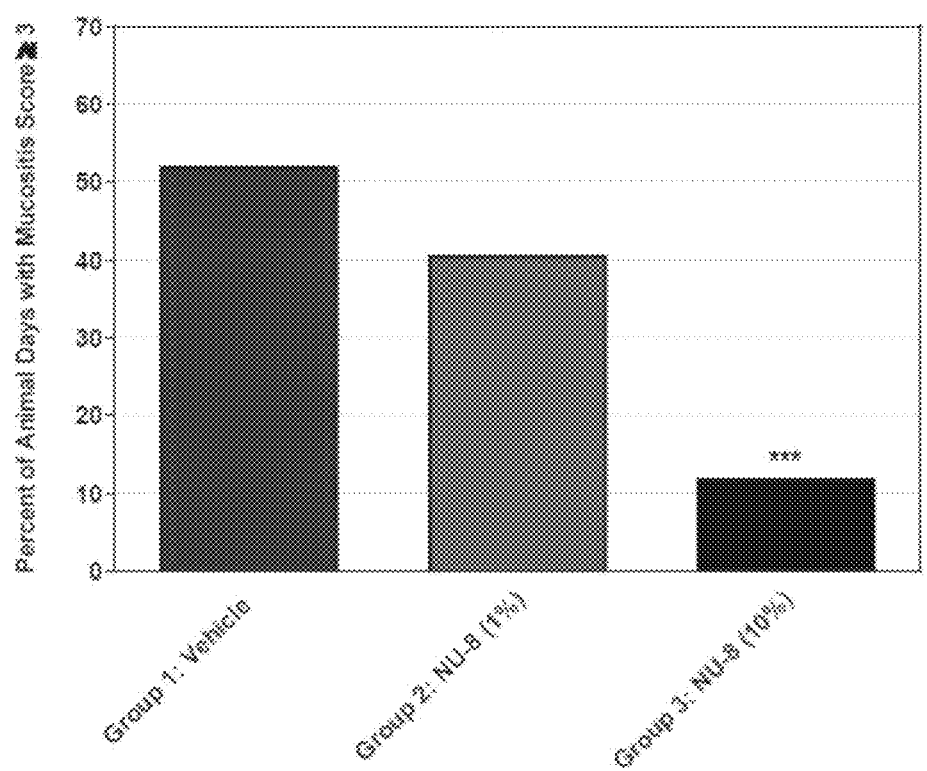
FIG. 4 shows percent of animal days with mucositis scores ≥3 for an entire study.

The significance of differences observed between the control and treatment groups were evaluated by comparing the days with mucositis scores ≥3 and <3 between groups using chi-square analysis. The results of this analysis are shown in Table 3 and FIG. 4 for the entire study duration (through Day 28). Over the course of the study (Table 3, FIG. 4), the percentage of animal days with a score of ≥3 in the Vehicle Group was 52.08%. The percentage of days with a score of ≥3 was statistically different for animals dosed with 10% Nu-8 in comparison to the Vehicle control group.

TABLE 3

| Chi-Square Analysis of Percent of Animal Days with a Mucositis Score ≥ 3 | | | | | | |
|---|---|---|---|---|---|---|
| Treatment | Days ≥ 3 | Days < 3 | Total Animal Days | % Days ≥ 3 | Chi Sq vs. Vehicle | P Value |
| Group 1: Vehicle (TID, Topical) | 50 | 46 | 96 | 52.08% | — | — |
| Group 2: Nu-8 (1%, TID, Topical) | 39 | 57 | 96 | 40.63% | 2.094 | 0.148 |
| Group 3: Nu-8 (10%, TID, Topical) | 10 | 74 | 84 | 11.90% | 30.762 | <0.001 |

To examine the levels of clinically significant mucositis, as defined by presentation with open ulcers (score ≥3), the total number of days in which an animal exhibited an elevated score was summed and expressed as a percentage of the total number of days scored for each group. Statistical significance of observed differences was calculated using chi-squared analysis.

Mucositis Severity

An analysis of the severity of mucositis was performed using the Mann-Whitney rank sum analysis to compare the visual mucositis scores for the treatment groups to the Vehicle control group on each day of evaluation. The results of this analysis are shown in Table 4. In this analysis, 2 days of significant reduction in the mucositis score are generally required before it is regarded as meaningful. Animals dosed with 1% Nu-8 (Group 2) displayed one day of significant improvement in mucositis scores compared to the Vehicle control group. Animals dosed with 10% Nu-8 (Group 3) demonstrated multiple days of significant improvement using this evaluation method.

TABLE 4

| A Comparison of Daily Mucositis Scores | | | | | | | | | | | | |
|---|---|---|---|---|---|---|---|---|---|---|---|---|
| | Rank Sum Analysts by Day | | | | | | | | | | | |
| Group | 6 | 8 | 10 | 12 | 14 | 16 | 18 | 20 | 22 | 24 | 26 | 28 |
| Vehicle vs. Nu-8 (1%) TID Topical | 1.0 | 1.0 | 1.0 | 0.4667 | *0.0406* | 0.6084 | 1.0 | 1.0 | 1.0 | 1.0 | 0.6084 | 0.6084 |
| Vehicle vs. Nu-8 (10%) TID Topical | 1.0 | 0.4667 | 1.0 | 1.0 | *0.0406* | 0.1319 | *0.0070* | *0.0070* | *0.0362* | *0.0319* | *0.0044* | *0.0109* |

The significance of group differences observed in daily mucositis scores was determined using the Mann-Whitney rank sum test. This nonparametric statistic is appropriate for the visual mucositis scoring scale. The p-values for each calculation are shown. Italicized font denotes decrease in mucositis scores compared to Vehicle Group (improvement of disease), bolded font denotes increase in mucositis scores (worsening of disease).

Percent of Animals with Ulcerative Mucositis by Day

The percentage of animals in each group with ulcerative mucositis at each day of evaluation is shown in Table 5. This evaluation was intended to clarify which days of treatment had its maximal impact on the course of ulcerative mucositis. There were numerous days where Nu-8 treatment, at both dose concentrations used in this study, had percent ulceration that was lower in comparison to vehicle-dosed animal (lower percent ulceration in comparison to vehicle can be interpreted as ameliorative of disease severity).

TABLE 5

| Percent of Animals with Ulceration by Day with Mucositis Score ≥ 3 | | | | | | | | | | | | |
|---|---|---|---|---|---|---|---|---|---|---|---|---|
| | Percent Ulceration by Day (Score ≥ 3) | | | | | | | | | | | |
| Group | 6 | 8 | 10 | 12 | 14 | 16 | 18 | 20 | 22 | 24 | 26 | 28 |
| Group 1: Vehicle (TID Topical) | 0.0 | 0.0 | 0.0 | 0.0 | 75.0 | 75.0 | 100.0 | 100.0 | 75.0 | 75.0 | 75.0 | 50.0 |
| Group 2: Nu-8 (1%, TID Topical) | 0.0 | 0.0 | 0.0 | 0.0 | *12.5* | *50.0* | *87.5* | 87.5 | 87.5 | *87.5* | *50.0* | *25.0* |
| Group 3: Nu-8 (10%, TID, Topical) | 0.0 | 0.0 | 0.0 | 0.0 | *12.5* | *25.0* | *25.0* | *25.0* | *25.0* | *12.5* | *0.0* | *0.0* |

To examine the levels of clinically significant mucositis, as defined by presentation with open ulcers (score ≥3), the percentage of animals from each treatment group that exhibited an open ulcer on each day of the study was determined. Italicized font denotes decrease in mucositis scores compared to Vehicle Group (improvement of disease), bolded font denotes increase in mucositis scores (worsening of disease).

Conclusions

1. There was one (1) unanticipated animal death during the study
2. Animals steadily gained weight throughout the duration of the study. In comparison to the vehicle group, animals in Group 3 exhibited statistically significant lower mean percent weight change (p<0.05) as determined by using Area-Under-the-Curve (AUC) analysis followed by evaluation with one-way ANOVA with Holm-Sidak's multiple comparisons post-hoc test.
3. There was modest attenuation of disease onset exhibited by animals in both groups treated with Nu-8, but more so in animals dosed with the 10% concentration (Group 3). Indeed, a robust mitigation of disease severity was exhibited by animals dosed with 10% Nu-8 in comparison to vehicle-dosed animals.
4. The percentage of animal days with a score of ≥3 in the Vehicle Group was 52.08%. The percentage of days with a score of ≥3 was significantly lower for animals dosed with 10% Nu-8 in comparison to the Vehicle control group.
5. Animals dosed with 1% Nu-8 (Group 2) displayed one day of significant improvement in mucositis scores compared to the Vehicle control group. Animals dosed with 10% Nu-8 (Group 3) demonstrated multiple days of significant improvement using this evaluation method.
6. There were numerous days where animals administered Nu-8 treatment, at both dose concentrations used in this study, had percent ulceration that was lower in comparison to vehicle-dosed animal (lower percent ulceration in comparison to vehicle can be interpreted as ameliorative of disease severity).

Example 4

Cellulose Gel Compounding

The following steps are used to prepare cellulose gels using a solution of Nu-3 as the free acid at the 100 g scale.

1. Add Nu-3 to a portion of the water and mix until homogeneous.
2. Add sodium chloride and mix until homogeneous.
3. Adjust pH to 1.5 (1.4-1.6 acceptable range) using 4% NaOH.
4. Add remaining water and mix until homogeneous.
5. Slowly add hydroxyethyl cellulose powder (Natrosol 250 HHX PH, Ashland) to the vortex of the mixing propeller.
6. Continue mixing until the polymer gel is transparent (~45-60 minutes).

Example 5

Fatty Alcohol (FA) Gel Compounding

The following steps are used to prepare FA gels using a solution of Nu-3 as the disodium salt at the 100 g scale.

1. Add Nu-3 to a portion of the water and mix until homogeneous.
2. Adjust pH to 1.5 (1.4-1.6 acceptable range) using 10% HCl.
3. Add remaining water and mix until homogeneous.
4. In a separate vessel combine cetostearyl alcohol (Crodacol CS 50 NF, Croda) and ceteareth-20 (Cetomacrogol 1000 NF, Croda) and heat to ~60° C. on a hot plate with mixing to melt the fatty alcohol and surfactant. Hold at ~60° C.
5. Heat API solution to ~60° C. on a hot plate while mixing with the propeller mixer.
6. Add fatty alcohol/surfactant mixture to the API solution while mixing with the propeller mixer. Remove propeller mixer, remove vessel from heat, and start high shear mixing.
7. Continue high shear mixing as the gel cools and thickens (~45-50° C.).
8. When the gel becomes too thick for mixing with the homogenizer, stop high shear mixing and continue mixing with the propeller mixer until the gel reaches 35-40° C.).

Example 6

Set-Up HPLC Assay and Autoclaving Study

The chromatography conditions in Table 6 are used to assay Nu-3 formulations for this Example.

TABLE 6

| Chromatography Conditions | |
| --- | --- |
| Column | Phenomenex Kinetex XB-C18 4.6 × 250 mm, 3.5 μm |
| Guard column | Phenomenx SecurityGuard cartridge, C18 (ODS) 4 mm L × 3 mm ID |
| Mobile Phase A | 10 mM ammonium acetate |
| Mobile Phase B | Acetonitrile |
| Gradient | 0.0 min. 95% A |
| | 20.0 min. 5% A |
| | 25.0 min. 5% A |
| | 25.1 min. 95% A |
| | 30.0 min. 95% A |
| Run Time | 30 min. |
| Flow Rate | 1.0 mL/min. |
| UV Detector | 265 nm |
| Injection Volume | 10 μL |
| Column Temperature | 30° C. |

Linearity is evaluated using Nu-3 solutions from 0.05 to 0.4 mg/mL. The correlation coefficient for peak area versus mg/mL has a value of 0.9994. The % Relative Standard Deviation (RSD) for repeated injections of a 0.2 mg/mL standard is <1.0%.

Example 7

Vehicle Gels for Evaluation

Three vehicle gels are prepared for evaluation. Sodium phosphate is used to simulate the presence of Nu-3 and benzyl alcohol is used as an antimicrobial preservative. Their compositions are summarized in Table 7.

TABLE 7

| Vehicle Gel Compositions | | | |
| --- | --- | --- | --- |
| | All Numbers are % w/w | | |
| Ingredient | Gel 1 | Gel 2 | Gel 3 |
| Sodium phosphate monobasic (monohydrate), USP | 0.4 | 0.4 | 0.4 |
| 3.5% HCl (q.s. to pH 2.5) | 0.9 | 0.9 | 0.9 |
| Sodium chloride, USP | 0.32 | 0.32 | 0.32 |
| Benzyl alcohol, NF | 0.5 | 0.5 | 0.5 |
| Natrosol HXX1250 NF | 1.00 | 1.75 | 0.0 |

TABLE 7-continued

Vehicle Gel Compositions

All Numbers are % w/w

| Ingredient | Gel 1 | Gel 2 | Gel 3 |
|---|---|---|---|
| Crodacol CS 50 NF | 0.0 | 0.0 | 4.0 |
| Cetomacrogol 1000 NF | 0.0 | 0.0 | 1.0 |
| Purified water, USP | q.s. to 100% | q.s. to 100% | q.s. to 100% |

Gels 2 and 3 are selected for formulation with Nu-3 at 5% w/w due to their superior physical properties. The formulation pH is reduced to a target value of 1.5 to ensure optimal activity of Nu-3.

Example 8

5% Nu-3 Cellulose Gel: Formulation and Stability
The composition for this gel is shown in Table 8.

TABLE 8

5% Cellulose Gel Composition

| Ingredient | All Numbers are % w/w 5% Nu-3 Cellulose Gel |
|---|---|
| Nu-3 20% solution | 25.0 |
| 4% NaOH (q.s. to pH 1.5) | 3.0 |
| Sodium chloride, USP | 0.32 |
| Natrosol HXX250 NF | 1.75 |
| Purified water, USP | q.s. to 100% |

The results for initial and stability results for the 5% Nu-3 cellulose gel are summarized in Table 9.

TABLE 9

Initial and Stability Results for the 5% Nu-3 Cellulose Gel

| Time Point/ Storage Condition | Assay, % w/w | Viscosity, cP[1] | Appearance | pH |
|---|---|---|---|---|
| Initial | 4.94 | 12,200 | Viscous Gel | 1.43 |
| 1 month, 40° C. | 4.90 | 125 | Liquid | 1.51 |
| 1 month, 30° C. | Not Tested | 4,600 | Liquid | Not Tested |
| 1 month, 25° C. | Not Tested | 6,870 | Slightly Viscous Liquid | Not Tested |
| 1 month, 5° C. | Not Tested | 11,200 | Viscous Gel | Not Tested |

[1]IRV viscometer, S14 spindle, 6R small sample adaptor, 30 rpm.

On storage, the cellulose Nu-3 gel's viscosity decreases significantly with temperature. This is likely due to hydrolysis of the cellulose in the polymer. However, the assay and pH after 1 month of storage at 40° C. has no significant change.

Example 9

5% Nu-3 FA Gel: Formulation and Stability
The composition for these gels are shown in Table 10.

TABLE 10

5% FA Gel Compositions

| Ingredient | Nu-3 FA Gel 1 | Nu-3 FA Gel 2 |
|---|---|---|
| Nu-3 disodium salt | 5.36 | 5.36 |
| 10% HCl (q.s. to pH 1.5) | 2.8 | 2.8 |

TABLE 10-continued

5% FA Gel Compositions

| Ingredient | Nu-3 FA Gel 1 | Nu-3 FA Gel 2 |
|---|---|---|
| Crodacol CS 50 NF | 4.0 | 7.25 |
| Cetomacrogol 1000 NF | 1.0 | 1.0 |
| Purified water, USP | q.s. to 100% | q.s. to 100% |

During Compounding, FA Gel 1 Fails to Thicken.

For FA Gel 2, the cetostearyl alcohol level is increased from 4.0 to 7.25 w/w. This increases the gel viscosity for the vehicle and the 5% Nu-3 formulations. The stability data for Nu-3 FA Gel 2 are summarized in Table 11.

TABLE 11

Initial and Stability Results for the 5% Nu-3 FA Gel 2

| Time Point/ Storage Condition | Assay, % w/w | Viscosity, cP[1] | Appearance | pH |
|---|---|---|---|---|
| Initial | 4.90 | 60,000 | Viscous, Off White Gel | 1.52 |
| 1 month, 40° C. | 4.96 | 74,000 | Viscous, Off White Gel | 1.45 |
| 1 month, 25° C. | 4.88 | 64,000 | Viscous, Off White Gel | 1.55 |

[1]IRV viscometer, S14 spindle, 6R small sample adaptor, 0.6 rpm.

The assay, appearance, and pH for FA Gel 2 shows no significant change after 1 month at 25 or 40° C. There is a slight increase in viscosity on storage, which is not uncommon for fatty alcohol gels. Their viscosities tend to level off after 1-3 months of storage.

Higher Strength Nu-3 FA Gels: Formulation and Stability
The composition for these gels are shown in Table 12 and the stability results are shown Table 13.

TABLE 12

FA Gel Compositions

All Numbers are % w/w

| Ingredient | 10% Nu-3 FA Gel | 15% Nu-3 FA Gel | 20% Nu-3 FA Gel |
|---|---|---|---|
| Nu-3 Disodium | 10.8 | 16.2 | 21.6 |
| 10% HCl (q.s. to pH 1.5) | 5.0 | 6.6 | 7.8 |
| Crodacol CS 50 NF[1] | 7.25 | 7.25 | 7.25 |
| Cetomacrogol 1000 NF[1] | 1.0 | 1.0 | 1.0 |
| Purified Water, USP | q.s. to 100% | q.s. to 100% | q.s. to 100% |

[1]Substitution of another vendor's grade of this excipient may cause a significant change in the formulation and is not recommend.

TABLE 13

Stability Results for the Nu-3 FA Gels

| Time Point/Storage Condition | | Asay, % w/w | Viscosity, cP[1] | Appearance[2] | pH |
|---|---|---|---|---|---|
| Initial | 10% | 10.3 | 63,500 | Conforms | 1.45 |
| | 15% | 14.6 | 65,200 | Conforms | 1.52 |
| | 20% | 19.9 | 71,000 | Conforms | 1.59 |
| 1 Month/40° C. | 10% | 10.2 | 85,600 | Conforms | 1.53 |
| | 15% | 14.7 | 89,000 | Conforms | 1.48 |
| | 20% | 20.1 | 84,400 | Conforms | 1.63 |
| 1 Month/25° C. | 10% | 10.1 | 66,900 | Conforms | 1.44 |
| | 15% | 14.6 | 69,000 | Conforms | 1.51 |
| | 20% | 19.8 | 72,400 | Conforms | 1.55 |

[1]IRV viscometer, S14 spindle, 6R small sample adaptor, 0.6 rpm.
[2]Off-white to tan viscous gel.

The assay, appearance, and pH for FA gels with 10-20% Nu-3 shows no significant change after 1 month at 25 or 40°

C. There is a slight increase in viscosity on storage, which is not uncommon for fatty alcohol gels. Their viscosities tend to level off after 1-3 months of storage.

Example 10

Nu-8 Treatment of Human Patient Having Oral Mucositis

A human patient is identified as having oral mucositis. A pharmaceutical composition in the form of a liquid solution containing an effective amount of Nu-8 is administered topically directly into the patient's oral cavity. The patient is monitored until symptoms are alleviated or ameliorated, and the pharmaceutical composition may be administered one or more additional times if it is determined that such administration is necessary or helpful for treatment.

While embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

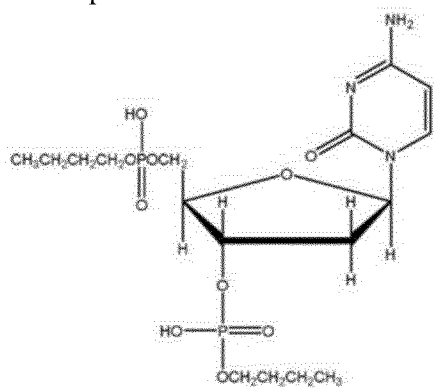

What is claimed is:

1. A method of treating oral mucositis in a patient in need thereof, the method comprising administering to the patient an effective amount of a compound having the formula:

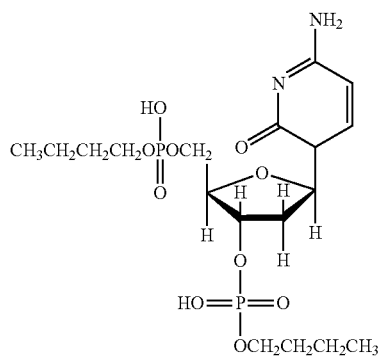

or a pharmaceutically acceptable salt thereof.

2. The method of claim 1, wherein the administration is topical administration.

3. The method of claim 2, wherein the topical administration is applied to the oral cavity of the patient.

4. The method of claim 1, wherein the administration is carried out using the compound, or a pharmaceutically acceptable salt thereof, in a gel, ointment, oil, solution, suspension, emulsion or other viscous composition.

5. The method of claim 1, wherein the administration is carried out using the compound, or a pharmaceutically acceptable salt thereof, in a mouthwash.

6. The method of claim 1, wherein the patient is administered at least one additional active ingredient.

7. The method of claim 1, wherein the compound, or a pharmaceutically acceptable salt thereof, is administered with a pharmaceutically acceptable carrier.

8. The method of claim 1, wherein the administration is carried out as a multiple dose regimen.

9. The method of claim 8, wherein the administration is carried out one or more times per day.

10. The method of claim 1, wherein the patient is a human.

11. A method of treating oral mucositis in a patient in need thereof, the method comprising topically administering to the oral cavity of the patient an effective amount of a pharmaceutical composition comprising a pharmaceutically acceptable carrier and a compound having the formula:

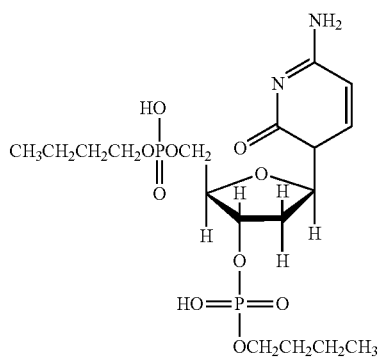

or a pharmaceutically acceptable salt thereof.

12. The method of claim 11, wherein the administration is carried out using the compound, or a pharmaceutically acceptable salt thereof, in a gel, ointment, oil, solution, suspension, emulsion or other viscous composition.

13. The method of claim 11, wherein the administration is carried out using the compound, or a pharmaceutically acceptable salt thereof, in a mouthwash.

14. The method of claim 11, wherein the compound, or a pharmaceutically acceptable salt thereof, is present in the pharmaceutical composition in an amount from about 1% to about 20% (weight/weight).

15. The method of claim 14, wherein the compound, or a pharmaceutically acceptable salt thereof, is present in the pharmaceutical composition in an amount from about 5% to about 15% (weight/weight).

16. The method of claim 11, wherein the compound, or a pharmaceutically acceptable salt thereof, is present in the pharmaceutical composition in an amount from about 30% to about 50% (weight/weight).

17. The method of claim 11, wherein the administration is carried out as a multiple dose regimen.

18. The method of claim 11, wherein the administration is carried out one or more times per day.

19. The method of claim 11, wherein the patient is a human.

20. The method of claim 11, wherein the pharmaceutical composition has a pH of about pH 1.5 to about pH 4.

21. The method of claim 11, wherein the pharmaceutical composition has a pH of about pH 3 to about pH 4.

* * * * *

UNITED STATES PATENT AND TRADEMARK OFFICE
CERTIFICATE OF CORRECTION

PATENT NO. : 11,123,357 B2
APPLICATION NO. : 16/656129
DATED : September 21, 2021
INVENTOR(S) : Steven A. Kates et al.

It is certified that error appears in the above-identified patent and that said Letters Patent is hereby corrected as shown below:

In the Claims

Column 41, Lines 32-46:

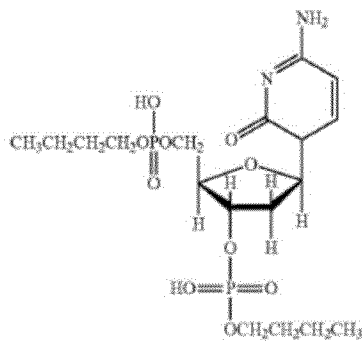

To be replaced with:

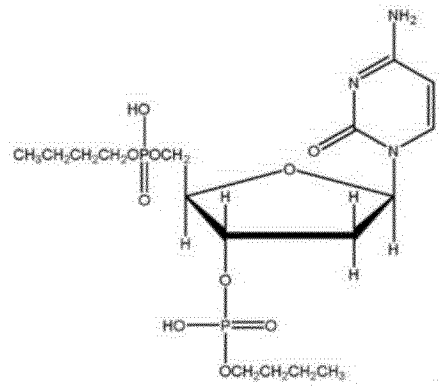

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,123,357 B2

Column 42, Lines 16-29:

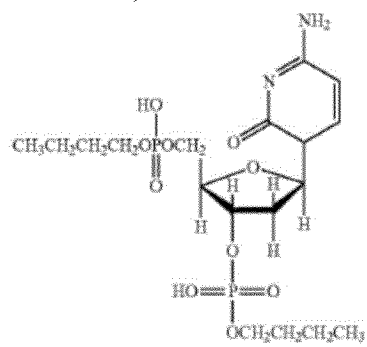

To be replaced with: